(12) United States Patent
Gavora et al.

(10) Patent No.: US 6,608,238 B1
(45) Date of Patent: Aug. 19, 2003

(54) TRANS-SOMATICS WITH GENE TRANSFER INTO MAMMARY EPITHELIAL CELLS

(75) Inventors: Jan S. Gavora, Ottawa (CA); Marcia M. Falconer, Nepean (CA); Thuy H. Nguyen, Ottawa (CA); Bernhard F. Benkel, Lethbridge (CA)

(73) Assignee: Gala Design Inc., Middleton, WI (US)

( * ) Notice: Subject to any disclaimer, the term of this patent is extended or adjusted under 35 U.S.C. 154(b) by 0 days.

(21) Appl. No.: 09/645,004

(22) Filed: Aug. 24, 2000

Related U.S. Application Data

(63) Continuation of application No. PCT/CA98/00607, filed on Jun. 25, 1998.

(30) Foreign Application Priority Data

Feb. 24, 1998 (CA) .............................................. 2224108

(51) Int. Cl.$^7$ .......................... C12P 21/00; C12P 21/06; A01N 63/00; C12N 15/63; C12N 15/00

(52) U.S. Cl. ....................... 800/21; 424/93.1; 424/93.2; 435/69.1; 435/455; 800/4

(58) Field of Search ................................ 435/455, 69.1; 514/44; 424/93.1, 93.2; 800/4, 21; 128/898

(56) References Cited

U.S. PATENT DOCUMENTS

| | | | |
|---|---|---|---|
| 5,215,904 A | 6/1993 | Gould et al. | ............. 435/172.3 |
| 5,700,657 A | * 12/1997 | Beaudry et al. | ............ 435/69.1 |

FOREIGN PATENT DOCUMENTS

| | | |
|---|---|---|
| WO | WO 95/15167 | 6/1995 |
| WO | WO 96/22379 | 4/1996 |

OTHER PUBLICATIONS

Culver et al., In Vivo Gene Transfer with Retroviral Vector–Producer Cells for Treatment of Experimental Brain Tumors, Jun. 12, 1992, Science, vol. 256, pp. 1550–1552.*
Tissue Plasminogen Activator for Acute Ischemic Stoke, Dec. 1995, The New England Journal of Medicine, vol. 333, No. 24, pp. 1581–1587.*
Joural of Investigative Medicine, Jan. 1998, vol. 46, No. 1, p. 69A.*
Jacomino et al, Gene Transfer into Fetal Rat Intestine, Sep. 10, 1996, Human Gene Therapy, vol. 7, pp. 1757–1762.*
Kim et al., Construction of Retrovrial Vectors with Improved Safety Gene Expression, and Versatility, Feb. 1998, Journal of Virology, pp. 994–1004.*
Gorewit et al., Effects of Duration of Udder Stimulation on Milking Dynamics and Oxytocin Release, 1985, J Dairy Sci., vol. 68, pp. 1813–1818.*
Aderson et al., Human gene therapy, Apr. 30, 1998, Nature, vol. 392, pp. 25–30.*

Cherkey et al., Adenal Chromaffin Cells on Microcarries Exhibit Enanced Long–Term Functional Effects when Implanted into the Mammalian Brian, 1996, Neuroscience, vol. 75, No. 2, p. 657–664.*
Zelenock et al., Improved retroviial transduction effeiciency jof vascular cell in vitro and in vivo during clinically relevent incubation periods using centrifugation . . . , Jul. 1997, Journal of Vascular Surgery, vol. 26, No. 1 pp. 119–127.*
Acher et al., Human growth hormone (hGH) secreton in milk of goats after direct transfer of the hGH gene . . . , Jul. 1994, Proc. Natl. Acad. Sci. USA, vol. 91, pp. 6840–6844.*
J.S. Archer et al., "Human growth hormone (hGH) secretion in milk of goats after direct transfer of the hGH gne into the mammary gland by using relication–defective retrovirus vectors". *Proc. Natl. Acad. Sci.* USA, 1994, vol. 91, pp. 6840–6844.
N.S. Yang et al., "Gene transfer into mamalian somatic cells in vivo", *Critical Reviews in Biotechnology*, vol. 12, No. 4, 1992, pp. 335–356.
K. W. Culver et al. "In vivo gene transfer with retroviral vector–producer cells for treatmnt of experimental brain tumors", *Science*, vol. 256, 1992, pp. 1550–1552.
C. Cepko, "Transduction of genes using retrovirus vectors", In: *Short Protocols in Moecular Biology*, 2$^{nd}$ Edition, Eds. F.M. Ausubel, R. Brent, R.E. Kingston, D.D. Moore, J.G. Seidman, J.A. Struhl, John Wiley & Sons, New York, NY, pp. 9–30 to 9–45, 1992.
P.A. Furth et al., "Gene transfer into somatic tisues by jet injection", *Analyt. Biochem*, 1992, vol. 205, pp. 365–368.
A.D. Miller et al., Use of retroviral vecotrs for gene transfer and expression, *Meth. Enzymol.*, vol. 217, pp. 581–599.
M.A. Morsy et al., "Safe gene vectors made simpler", *Nature Biotech.*, 1997, vol. 15, p. 17.
D. Pennica et al., Cloning and expression of human tissue–type plaminogen activator cDNA in *E. coli, Nature*, vol. 301, pp. 214–221.

(List continued on next page.)

*Primary Examiner*—Shin-Lin Chen
(74) *Attorney, Agent, or Firm*—Medlen & Carroll, LLP.

(57) ABSTRACT

A method is described to transfer a gene encoding a valuable compound, such as a pharmaceutical, into the secretory cells of the mammary gland to produce a new compound into the milk or to alter the composition of the milk. In this method the packaging cell line producing the viral-derived particles is infused into the mammary gland. The packaging cells will attach and survive for a period of time within the mammary gland. While the cells are viable, they will supply a continuous source of viral-derived particles to trans-infect the maximum number of mammary epithelial cells. After a period of time in the mammary gland, both the particles and the packaging cells will be destroyed by natural mechanisms while the trans-infected mammary epithelial cells continue to express gene(s) encoding the valuable compound or gene(s) to alter the composition of the milk.

20 Claims, 2 Drawing Sheets

OTHER PUBLICATIONS

A.R. Thierry et al., "Systemic gene therapy: Biodistribution and long–term expression of a transgene in mice", *Proc. Natl. Acad. Sci. USA*, vol. 92, pp. 9742–9746.

N.S. Yang et al., "Gene transfer into mamalian somatic cells in vivo", *Critical Reviews in Biotechnology* 12:335–356 (1992).

C. Cepko, "Transduction of genes using retrovirus vectors," In: *Short Protocols In Molecular Biology* 2nd Ed., pp. 930–945 (1992).

P.A. Furth et al., "Gene transfer into somatic tissues by joint injection", *Analyt. Biochem.* 205:365–368 (1992).

A.D. Miller et al., "Useof retroviral vectors for gene transfer and expression", *Meth. Enzymol.* 217:581–599 (1993).

M.A. Morsy et al., "Safe gene vectors made simpler", *Nature Biotech.* 15:17 (1997).

D. Pennica et al., "Cloning and expression of human tissue–type plaminogen activator cDNA in *E. coli*", *Nature* 301:214–221 (1983).

A.R. Thierry et al., "Systmic gene therapy: Biodistribution and long–term expression of a transgene in mice", *PNAC* 92:9742–9746 (1995).

* cited by examiner

SEQUENCE LISTING

<160> NUMBER OF SEQ ID NOS: 4

<210> SEQ ID NO 1
<211> LENGTH: 7699
<212> TYPE: DNA
<213> ORGANISM: Artificial
<220> FEATURE:
<223> OTHER INFORMATION: Plasmid pLAiN

<400> SEQUENCE: 1

| | | | | | |
|---|---|---|---|---|---|
| gaattgctag | caattgctag | caattgctag | caattcatac | cagatcaccg | aaaactgtcc | 60 |
| tccaaatgtg | tccccctcac | actcccaaat | tcgcgggctt | ctgcctctta | gaccactcta | 120 |
| ccctattccc | cacactcacc | ggagccaaag | ccgcggccct | tccgtttctt | tgcttttgaa | 180 |
| agacccacc | cgtaggtggc | aagctagctt | aagtaacgcc | actttgcaag | gcatggaaaa | 240 |
| atacataact | gagaatagaa | aagttcagat | caaggtcagg | aacaaagaaa | cagctgaata | 300 |
| ccaaacagga | tatctgtggt | aagcggttcc | tgccccggct | cagggccaag | aacagatgag | 360 |
| acagctgagt | gatgggccaa | acaggatatc | tgtggtaagc | agttcctgcc | ccggctcggg | 420 |
| gccaagaaca | gatggtcccc | agatgcggtc | cagccctcag | cagtttctag | tgaatcatca | 480 |
| gatgtttcca | gggtgcccca | aggacctgaa | aatgaccctg | taccttattt | gaactaacca | 540 |
| atcagttcgc | ttctcgcttc | tgttcgcgcg | cttccgctct | ccgagctcaa | taaaagagcc | 600 |
| cacaacccct | cactcggcgc | gccagtcttc | cgatagactg | cgtcgcccgg | gtacccgtat | 660 |
| tcccaataaa | gcctcttgct | gtttgcatcc | gaatcgtggt | ctcgctgttc | cttgggaggg | 720 |
| tctcctctga | gtgattgact | acccacgacg | ggggtctttc | atttgggggc | tcgtccggga | 780 |
| tttggagacc | cctgcccagg | gaccaccgac | ccaccaccgg | gaggtaagct | ggccagcaac | 840 |
| ttatctgtgt | ctgtccgatt | gtctagtgtc | tatgtttgat | gttatgcgcc | tgcgtctgta | 900 |
| ctagttagct | aactagctct | gtatctggcg | gacccgtggt | ggaactgacg | agttctgaac | 960 |
| acccggccgc | aaccctggga | gacgtccag | ggactttggg | ggccgttttt | gtggcccgac | 1020 |
| ctgaggaagg | gagtcgatgt | ggaatccgac | cccgtcagga | tatgtggttc | tggtaggaga | 1080 |
| cgagaaccta | aaacagttcc | cgcctccgtc | tgaattttg | ctttcggttt | ggaaccgaag | 1140 |
| ccgcgcgtct | tgtctgctgc | agcgctgcag | catcgttctg | tgttgtctct | gtctgactgt | 1200 |
| gtttctgtat | ttgtctgaaa | attagggcca | gactgttacc | actcccttaa | gtttgacctt | 1260 |
| aggtcactgg | aaagatgtcg | agcggatcgc | tcacaaccag | tcggtagatg | tcaagaagag | 1320 |
| acgttgggtt | accttctgct | ctgcagaatg | gccaaccttt | aacgtcggat | ggccgcgaga | 1380 |
| cggcaccttt | aaccgagacc | tcatcaccca | ggttaagatc | aaggtctttt | cacctggccc | 1440 |
| gcatggacac | ccagaccagg | tcccctacat | cgtgacctgg | gaagccttgg | cttttgaccc | 1500 |
| ccctccctgg | gtcaagccct | ttgtacaccc | taagcctccg | cctcctcttc | ctccatccgc | 1560 |
| cccgtctctc | cccttgaac | ctcctcgttc | gaccccgcct | cgatcctccc | tttatccagc | 1620 |
| cctcactcct | tctctaggcg | ccggaattcg | ttaactcgac | atggaagtcc | ttctcctcct | 1680 |
| cgcagctgtc | gggcttttgct | gggcacagta | caatcccaac | actcaggctg | gaggacatc | 1740 |
| tatcgtgcat | ctctttgaat | ggcgctgggc | cgacattgca | ctggagtgcg | aacactattt | 1800 |
| agctcctaat | gggtttggag | gagttcaggt | ttctcctcca | aatgaaaaca | ttgtcattac | 1860 |
| taatccgaac | aggccctggt | gggaaagata | ccagcccatc | agctacaaga | tctgcagtcg | 1920 |
| atcgggcaat | gaaaatgaat | tcagagacat | ggtgaccaga | tgcaacaatg | ttggagttcg | 1980 |

```
tatttatgtg gatgctgttg tcaatcacat gtgtggatct atgggtggca cgggcaccca  2040
ctcaacatgt gggagctatt tcaacaccgg gactagagat tttcccgctg tgccgtactc  2100
tgcctgggat ttcaatgacg gcaaatgtca cactgcaagt ggagacatcg aaaattatgg  2160
ggacatgtat caggtccggg attgcaagtt gtccagcctt cttgatctgg ctctggagaa  2220
ggactatgta cgctcaacaa ttgcagcgta catgaatcac ctcattgata tgggtgtagc  2280
agggttccgg atcgatgctg ccaagcatat gtggccaggg gacataagag cgtttctgga  2340
caaactgcac gatctaaata ctcagtggtt ttcagcagga acgaaaccct ttatttacca  2400
agaggtaatt gacttgggag agagccaat cacaggcagt cagtactttg ggaatggccg  2460
cgtgacagaa ttcaagtatg gtgccaaact ggggacggtg atccggaagt ggaatggaga  2520
gaagatggcc tacttaaaga actggggaga aggctggggc tttgtgcctt ctgacagagc  2580
cctggtgttt gtggataacc acgacaacca gcggggcac gggcaggcg agcttccat  2640
tcttactttc tgggatgcca ggctttataa aatggcggtt ggtttcatgc tcgctcatcc  2700
gtacgggttc acacgggtga tgtcaagtta tcgttggcca agatatttcg aaaacggagt  2760
ggatgttaac gactgggtgg gaccaccaag taactcggac ggatcgacga agtccgttac  2820
aatcaacgca gacactacct gtggcaatga ctgggtctgc gaacatcgct ggcgacaaat  2880
aaggaacatg gttatcttcc gtaatgtggt agacggtcag cctttctcaa actggtggga  2940
caacgggagc aatcaagtag ctttcggtcg cggcgacaga ggcttcattg tctttaataa  3000
tgatgactgg tatatgaatg tcgatttgca aactggtctg cctgctggaa cctactgcga  3060
tgttatttct ggacaaaagg aaggcagtgc gtgtactgga aagcaggtgt acgtttcctc  3120
ggatggaaag gccaatttcc agattagtaa cagcgatgaa gatccatttg ttgcaattca  3180
cgttgatgcc aagttataag cttcgaggat ccactagtaa cggccgccag tgtgctggaa  3240
ttcggcttgt cgacatctag ggcggccaat tccgcccctc tcccccccc cctaacgtt  3300
actggccgaa gccgcttgga ataaggccgg tgtgtgtttg tctatatgtg attttccacc  3360
atattgccgt cttttggcaa tgtgagggcc cggaaacctg gccctgtctt cttgacgagc  3420
attcctaggg gtctttcccc tctcgccaaa ggaatgcaag gtctgttgaa tgtcgtgaag  3480
gaagcagttc ctctggaagc ttcttgaaga caaacaacgt ctgtagcgac cctttgcagg  3540
cagcggaacc ccccacctgg cgacaggtgc ctctgcggcc aaaagccacg tgtataagat  3600
acacctgcaa aggcggcaca accccagtgc cacgttgtga gttggatagt tgtggaaaga  3660
gtcaaatggc tctcctcaag cgtagtcaac aaggggctga aggatgccca gaaggtaccc  3720
cattgtatgg gaatctgatc tggggcctcg gtgcacatgc tttacatgtg tttagtcgag  3780
gttaaaaaag ctctaggccc cccgaaccac ggggacgtgg ttttcctttg aaaaacacga  3840
tgataagctt gccacaaccc gggataattc ctgcagccaa tatgggatcg ccattgaac  3900
aagatggatt gcacgcaggt tctccggccg cttgggtgga gaggctattc ggctatgact  3960
gggcacaaca gacaatcggc tgctctgatg ccgccgtgtt ccggctgtca gcgcaggggc  4020
gcccggttct ttttgtcaag accgacctgt ccggtgccct gaatgaactg caggacgagg  4080
cagcgcggct atcgtggctg gccacgacgg gcgttccttg cgcagctgtg ctcgacgttg  4140
tcactgaagc gggaagggac tggctgctat tgggcgaagt gccggggcag gatctcctgt  4200
catctcacct tgctcctgcc gagaaagtat ccatcatggc tgatgcaatg cggcggctgc  4260
atacgcttga tccggctacc tgcccattcg accaccaagc gaaacatcgc atcgagcgag  4320
```

-continued

```
cacgtactcg gatggaagcc ggtcttgtcg atcaggatga tctggacgaa gagcatcagg    4380
ggctcgcgcc agccgaactg ttcgccaggc tcaaggcgcg catgcccgac ggcgatgatc    4440
tcgtcgtgac ccatggcgat gcctgcttgc cgaatatcat ggtggaaaat ggccgctttt    4500
ctggattcat cgactgtggc cggctgggtg tggcggaccg ctatcaggac atagcgttgg    4560
ctacccgtga tattgctgaa gagcttggcg gcgaatgggc tgaccgcttc ctcgtgcttt    4620
acggtatcgc cgctcccgat tcgcagcgca tcgccttcta tcgccttctt gacgagttct    4680
tctgagcggg actctggggt tcgataaaat aaaagatttt atttagtctc cagaaaaagg    4740
ggggaatgaa agaccccacc tgtaggtttg gcaagctagc ttaagtaacg ccattttgca    4800
aggcatggaa aatacataa ctgagaatag agaagttcag atcaaggtca ggaacagatg    4860
gaacagctga atatgggcca aacaggatat ctgtggtaag cagttcctgc cccggctcag    4920
ggccaagaac agatgaaca gctgaatatg ggccaaacag gatatctgtg gtaagcagtt    4980
cctgccccgg ctcagggcca agaacagatg gtccccagat gcggtccagc cctcagcagt    5040
ttctagagaa ccatcagatg tttccagggt gccccaagga cctgaaatga ccctgtgcct    5100
tatttgaact aaccaatcag ttcgcttctc gcttctgttc gcgcgcttct gctccccgag    5160
ctcaataaaa gagcccacaa ccctcactc ggggcgccag tcctccgatt gactgagtcg    5220
cccgggtacc cgtgtatcca ataaaccctc ttgcagttgc atccgacttg tggtctcgct    5280
gttccttggg agggtctcct ctgagtgatt gactacccgt cagcgggggt ctttcatttg    5340
ggggctcgtc cgggatcggg agaccctgc ccagggacca ccgacccacc accgggaggt    5400
aagctggctg cctcgcgcgt ttcggtgatg acggtgaaaa cctctgacac atgcagctcc    5460
cggagacggt cacagcttgt ctgtaagcgg atgccggag cagacaagcc cgtcagggcg    5520
cgtcagcggg tgttggcggg tgtcggggcg cagccatgac ccagtcacgt agcgatagcg    5580
gagtgtatac tggcttaact atgcggcatc agagcagatt gtactgagag tgcaccatat    5640
gcggtgtgaa ataccgcaca gatgcgtaag gagaaaatac cgcatcaggc gctcttccgc    5700
ttcctcgctc actgactcgc tgcgctcggt cgttcggctg cggcgagcgg tatcagctca    5760
ctcaaaggcg gtaatacggt tatccacaga atcagggat aacgcaggaa agaacatgtg    5820
agcaaaaggc cagcaaaagg ccaggaaccg taaaaaggcc gcgttgctgg cgttttccca    5880
taggctccgc cccctgacg agcatcacaa aaatcgacgc tcaagtcaga ggtggcgaaa    5940
cccgacagga ctataaagat accaggcgtt tccccctgga agctccctcg tgcgctctcc    6000
tgttccgacc ctgccgctta ccggatacct gtccgccttt ctcccttcgg gaagcgtggc    6060
gctttctcat agctcacgct gtaggtatct cagttcggtg taggtcgttc gctccaagct    6120
gggctgtgtg cacgaacccc ccgttcagcc cgaccgctgc gccttatccg gtaactatcg    6180
tcttgagtcc aacccggtaa gacacgactt atcgccactg gcagcagcca ctggtaacag    6240
gattagcaga gcgaggtatg taggcggtgc tacagagttc ttgaagtggt ggcctaacta    6300
cggctacact agaaggacag tatttggtat ctgcgctctg ctgaagccag ttaccttcgg    6360
aaaaagagtt ggtagctctt gatccggcaa acaaaccacc gctggtagcg tggttttttt    6420
tgtttgcaag cagcagatta cgcgcagaaa aaaggatct caagaagatc ctttgatctt    6480
ttctacgggg tctgacgctc agtggaacga aaactcacgt taagggattt tggtcatgag    6540
attatcaaaa aggatcttca cctagatcct tttaaattaa aaatgaagtt ttaaatcaat    6600
ctaaagtata tatgagtaaa cttggtctga cagttaccaa tgcttaatca gtgaggcacc    6660
tatctcagcg atctgtctat ttcgttcatc catagttgcc tgactccccg tcgtgtagat    6720
```

-continued

```
aactacgata cgggagggct taccatctgg ccccagtgct gcaatgatac cgcgagaccc      6780
acgctcaccg gctccagatt tatcagcaat aaaccagcca gccggaaggg ccgagcgcag      6840
aagtggtcct gcaactttat ccgcctccat ccagtctatt aattgttgcc gggaagctag      6900
agtaagtagt tcgccagtta atagtttgcg caacgttgtt gccattgctg caggcatcgt      6960
ggtgtcacgc tcgtcgtttg gtatggcttc attcagctcc ggttcccaac gatcaaggcg      7020
agttacatga tcccccatgt tgtgcaaaaa agcggttagc tccttcggtc ctccgatcgt      7080
tgtcagaagt aagttggccg cagtgttatc actcatggtt atggcagcac tgcataattc      7140
tcttactgtc atgccatccg taagatgctt ttctgtgact ggtgagtact caaccaagtc      7200
attctgagaa tagtgtatgc ggcgaccgag ttgctcttgc ccggcgtcaa cacgggataa      7260
taccgcgcca catagcagaa ctttaaaagt gctcatcatt ggaaaacgtt cttcggggcg      7320
aaaactctca aggatcttac cgctgttgag atccagttcg atgtaaccca ctcgtgcacc      7380
caactgatct tcagcatctt ttactttcac cagcgtttct gggtgagcaa aaacaggaag      7440
gcaaaatgcc gcaaaaaagg gaataagggc gacacgaaaa tgttgaatac tcatactctt      7500
cctttttcaa tattattgaa gcatttatca gggttattgt ctcatgagcg gatacatatt      7560
tgaatgtatt tagaaaaata aacaaatagg ggttccgcgc acatttcccc gaaaagtgcc      7620
acctgacgtc taagaaacca ttattatcat gacattaacc tataaaaata ggcgtatcac      7680
gaggcccttt cgtcttcaa                                                    7699

<210> SEQ ID NO 2
<211> LENGTH: 7980
<212> TYPE: DNA
<213> ORGANISM: Artificial
<220> FEATURE:
<223> OTHER INFORMATION: Plasmid pLAiH

<400> SEQUENCE: 2
gaattgctag caattgctag caattgctag caattcatac cagatcaccg aaaactgtcc        60
tccaaatgtg tcccctcac actcccaaat tcgcgggctt ctgcctctta gaccactcta       120
ccctattccc cacactcacc ggagccaaag ccgcggccct tccgtttctt tgcttttgaa       180
agaccccacc cgtaggtggc aagctagctt aagtaacgcc actttgcaag gcatggaaaa       240
atacataact gagaatagaa aagttcagat caaggtcagg aacaaagaaa cagctgaata       300
ccaaacagga tatctgtggt aagcggttcc tgccccggct cagggccaag aacagatgag       360
acagctgagt gatgggccaa acaggatatc tgtggtaagc agttcctgcc ccggctcggg       420
gccaagaaca gatggtcccc agatgcggtc cagccctcag cagtttctag tgaatcatca       480
gatgtttcca gggtgcccca aggacctgaa aatgaccctg taccttattt gaactaacca       540
atcagttcgc ttctcgcttc tgttcgcgcg cttccgctct ccgagctcaa taaaagagcc       600
cacaacccct cactcggcgc gccagtcttc cgatagactg cgtcgcccgg gtacccgtat       660
tcccaataaa gcctcttgct gtttgcatcc gaatcgtggt ctcgctgttc cttgggaggg       720
tctcctctga gtgattgact acccacgacg ggggtctttc atttgggggc tcgtccggga       780
tttggagacc cctgcccagg gaccaccgac ccaccaccgg gaggtaagct ggccagcaac       840
ttatctgtgt ctgtccgatt gtctagtgtc tatgtttgat gttatgcgcc tgcgtctgta       900
ctagttagct aactagctct gtatctggcg gacccgtggt ggaactgacg agttctgaac       960
acccggccgc aacccctggga gacgtcccag ggactttggg ggccgttttt gtggcccgac      1020
```

```
ctgaggaagg gagtcgatgt ggaatccgac cccgtcagga tatgtggttc tggtaggaga    1080
cgagaaccta aaacagttcc cgcctccgtc tgaattttg ctttcggttt ggaaccgaag     1140
ccgcgcgtct tgtctgctgc agcgctgcag catcgttctg tgttgtctct gtctgactgt    1200
gtttctgtat ttgtctgaaa attagggcca gactgttacc actcccttaa gtttgacctt    1260
aggtcactgg aaagatgtcg agcggatcgc tcacaaccag tcggtagatg tcaagaagag    1320
acgttgggtt accttctgct ctgcagaatg gccaacctt aacgtcggat ggccgcgaga     1380 cggcacctt aaccgagacc tcatcaccca ggttaagatc aaggtctttt cacctggccc     1440
gcatggacac ccagaccagg tcccctacat cgtgacctgg gaagccttgg cttttgaccc    1500
ccctccctgg gtcaagccct tgtacaccc taagcctccg cctcctcttc ctccatccgc     1560
cccgtctctc ccccttgaac tcctcgttc gaccccgcct cgatcctccc tttatccagc     1620
cctcactcct tctctaggcg ccggaattcg ttaactcgac atggaagtcc ttctcctcct    1680
ctcagctgtc gggctttgct gggcacagta caatcccaac actcaggctg ggaggacatc    1740
tatcgtgcat ctcttgaat ggcgctgggc cgacattgca ctggagtgcg aacactattt     1800
agctcctaat gggtttggag gagttcaggt ttctcctcca aatgaaaaca ttgtcattac    1860
taatccgaac aggccctggt gggaaagata ccagcccatc agctacaaga tctgcagtcg    1920
atcgggcaat gaaaatgaat tcagagacat ggtgaccaga tgcaacaatg ttggagttcg    1980
tatttatgtg gatgctgttg tcaatcacat gtgtggatct atgggtggca cgggcaccca    2040
ctcaacatgt gggagctatt tcaacaccgg gactagagat tttcccgctg tgccgtactc    2100
tgcctgggat ttcaatgacg gcaaatgtca cactgcaagt ggagacatcg aaaattatgg    2160
ggacatgtat caggtccggg attgcaagtt gtccagcctt cttgatctgg ctctggagaa    2220
ggactatgta cgctcaacaa ttgcagcgta catgaatcac ctcattgata gggtgtagc     2280 agggttccgg atcgatgctg ccaagcatat gtggccaggg gacataagag cgtttctgga    2340
caaactgcac gatctaaata ctcagtggtt ttcagcagga acgaaaccct ttatttacca    2400
agaggtaatt gacttgggag gagagccaat cacaggcagt cagtactttg ggaatggccg    2460
cgtgacagaa ttcaagtatg gtgccaaact ggggacggtg atccggaagt ggaatggaga    2520
gaagatggcc tacttaaaga actggggaga aggctgggc tttgtgcctt ctgacagagc     2580
cctggtgttt gtggataacc acgacaacca gcggggcac ggggcaggcg gagcttccat     2640
tcttactttc tgggatgcca ggctttataa aatggcggtt ggtttcatgc tcgctcatcc    2700
gtacgggttc acacgggtga tgtcaagtta tcgttggcca agatatttcg aaaacggagt    2760
ggatgttaac gactgggtgg gaccaccaag taactcggac ggatcgacga agtccgttac    2820
aatcaacgca gacactacct gtggcaatga ctgggtctgc aacatcgct ggcgacaaat     2880 aaggaacatg gttatcttcc gtaatgtggt agacggtcag ccttctcaa actggtggga    2940 caacgggagc aatcaagtag ctttcggtcg cggcgacaga ggcttcattg tctttaataa    3000
tgatgactgg tatatgaatg tcgatttgca aactggtctg cctgctggaa cctactgcga    3060
tgttatttct ggacaaaagg aaggcagtgc gtgtactgga aagcaggtgt acgtttcctc    3120
ggatggaaag gccaatttcc agattagtaa cagcgatgaa gatccatttg ttgcaattca    3180
cgttgatgcc aagttataag cttcgaggat ccactagtaa cggccgccag tgtgctggaa    3240
ttcggcttgt cgacatctag gcggccaat tccgccctc tcccccccc cctaacgtt       3300 actgccgaa gccgcttgga ataaggccgg tgtgtgtttg tctatatgtg attttccacc     3360
atattgccgt cttttggcaa tgtgagggcc cggaaacctg gccctgtctt cttgacgagc    3420
```

-continued

```
attcctaggg gtctttcccc tctcgccaaa ggaatgcaag gtctgttgaa tgtcgtgaag    3480
gaagcagttc ctctggaagc ttcttgaaga caaacaacgt ctgtagcgac cctttgcagg    3540
cagcggaacc ccccacctgg cgacaggtgc ctctgcggcc aaaagccacg tgtataagat    3600
acacctgcaa aggcggcaca accccagtgc cacgttgtga gttggatagt tgtggaaaga    3660
gtcaaatggc tctcctcaag cgtagtcaac aaggggctga aggatgccca gaaggtaccc    3720
cattgtatgg gaatctgatc tggggcctcg gtgcacatgc tttacatgtg tttagtcgag    3780
gttaaaaaag ctctaggccc cccgaaccac ggggacgtgg ttttcctttg aaaaacacga    3840
tgataagctt gccacaaccc aaacagcgtc aacagcgtgc cgcagatccc gggcaatgag    3900
atatgaaaaa gcctgaactc accgcgacgt ctgtcgagaa gtttctgatc gaaagttcg    3960 acagcgtctc cgacctgatg cagctctcgg agggcgaaga atctcgtgct ttcagcttcg    4020
atgtaggagg gcgtggatat gtcctgcggg taaatagctg cgccgatggt ttctacaaag    4080
atcgttatgt ttatcggcac tttgcatcgg ccgcgctccc gattccggaa gtgcttgaca    4140
ttggggaatt cagcgagagc ctgacctatt gcatctcccg ccgtgcacag ggtgtcacgt    4200
tgcaagacct gcctgaaacc gaactgcccg ctgttctgca gccggtcgcg gaggccatgg    4260
atgcgatcgc tgcggccgat cttagccaga cgagcgggtt cggcccattc ggaccgcaag    4320
gaatcggtca atacactaca tggcgtgatt tcatatgcgc gattgctgat ccccatgtgt    4380
atcactggca aactgtgatg gacgacaccg tcagtgcgtc cgtcgcgcag gctctcgatg    4440
agctgatgct ttgggccgag gactgccccg aagtccggca cctcgtgcac gcggatttcg    4500
gctccaacaa tgtcctgacg acaatggcc gcataacagc ggtcattgac tggagcgagg    4560
cgatgttcgg ggattcccaa tacgaggtcg ccaacatctt cttctggagg ccgtggttgg    4620
cttgtatgga gcagcagacg cgctacttcg agcggaggca tccggagctt gcaggatcgc    4680
cgcggctccg ggcgtatatg ctccgcattg gtcttgacca actctatcag agcttggttg    4740
acggcaattt cgatgatgca gcttgggcgc agggtcgatg cgacgcaatc gtccgatccg    4800
gagccgggac tgtcggcgt acacaaatcg cccgcagaag cgcggccgtc tggaccgatg    4860
gctgtgtaga agtactcgcc gatagtggaa accgacgccc cagcactcgt ccgagggcaa    4920 aggaatagg gagatggggg aggctaactg aaacacggaa gggcccgcgg gactctgggg    4980
ttcgataaaa taaagatttt tatttagtct ccagaaaaag gggggaatga agaccccac     5040 ctgtaggttt ggcaagctag cttaagtaac gccattttgc aaggcatgga aaatacata    5100 actgagaata gagaagttca gatcaaggtc aggaacagat ggaacagctg aatatgggcc    5160
aaacaggata tctgtggtaa gcagttcctg ccccggctca gggccaagaa cagatggaac    5220
agctgaatat gggccaaaca ggatatctgt ggtaagcagt tcctgccccg gctcagggcc    5280
aagaacagat ggtccccaga tgcggtccag ccctcagcag tttctagaga accatcagat    5340
gtttccaggg tgccccaagg acctgaaatg accctgtgcc ttatttgaac taaccaatca    5400
gttcgcttct cgcttctgtt cgcgcgcttc tgctccccga gctcaataaa agagcccaca    5460 accctcact cggggcgcca gtcctccgat tgactgagtc gcccgggtac ccgtgtatcc    5520
aataaaccct cttgcagttg catccgactt gtggtctcgc tgttccttgg gagggtctcc    5580
tctgagtgat tgactacccg tcagcggggg tctttcattt ggggctcgt ccgggatcgg    5640 gagacccctg cccagggacc accgacccac caccggagg taagctggct gcctcgcgcg    5700
tttcggtgat gacggtgaaa acctctgaca catgcagctc ccggagacgg tcacagcttg    5760
```

-continued

```
tctgtaagcg gatgccggga gcagacaagc ccgtcagggc gcgtcagcgg gtgttggcgg      5820
gtgtcgggge gcagccatga cccagtcacg tagcgatagc ggagtgtata ctggcttaac      5880
tatgcggcat cagagcagat tgtactgaga gtgcaccata tgcggtgtga aataccgcac      5940
agatgcgtaa ggagaaaata ccgcatcagg cgctcttccg cttcctcgct cactgactcg      6000
ctgcgctcgg tcgttcggct gcggcgagcg gtatcagctc actcaaaggc ggtaatacgg      6060
ttatccacag aatcagggga taacgcagga agaacatgt gagcaaaagg ccagcaaaag      6120
gccaggaacc gtaaaaaggc cgcgttgctg gcgtttttcc ataggctccg cccccctgac      6180
gagcatcaca aaaatcgacg ctcaagtcag aggtggcgaa acccgacagg actataaaga      6240
taccaggcgt ttccccctgg aagctccctc gtgcgctctc ctgttccgac cctgccgctt      6300
accggatacc tgtccgcctt tctcccttcg ggaagcgtgg cgctttctca tagctcacgc      6360
tgtaggtatc tcagttcggt gtaggtcgtt cgctccaagc tgggctgtgt gcacgaaccc      6420
cccgttcagc ccgaccgctg cgccttatcc ggtaactatc gtcttgagtc caacccggta      6480
agacacgact tatcgccact ggcagcagcc actggtaaca ggattagcag agcgaggtat      6540
gtaggcggtg ctacagagtt cttgaagtgg tggcctaact acggctacac tagaaggaca      6600
gtatttggta tctgcgctct gctgaagcca gttaccttcg gaaaaagagt ggtagctct      6660
tgatccggca aacaaaccac cgctggtagc ggtggttttt ttgtttgcaa gcagcagatt      6720
acgcgcagaa aaaaggatc tcaagaagat cctttgatct tttctacggg gtctgacgct      6780
cagtggaacg aaaactcacg ttaagggatt ttggtcatga gattatcaaa aaggatcttc      6840
acctagatcc ttttaaatta aaaatgaagt tttaaatcaa tctaaagtat atatgagtaa      6900
acttggtctg acagttacca atgcttaatc agtgaggcac ctatctcagc gatctgtcta      6960
tttcgttcat ccatagttgc ctgactcccc gtcgtgtaga taactacgat acgggagggc      7020
ttaccatctg gccccagtgc tgcaatgata ccgcgagacc cacgctcacc ggctccagat      7080
ttatcagcaa taaaccagcc agccggaagg gccgagcgca gaagtggtcc tgcaacttta      7140
tccgcctcca tccagtctat taattgttgc cgggaagcta gagtaagtag ttcgccagtt      7200
aatagtttgc gcaacgttgt tgccattgct gcaggcatcg tggtgtcacg ctcgtcgttt      7260
ggtatggctt cattcagctc cggttcccaa cgatcaaggc gagttacatg atcccccatg      7320
ttgtgcaaaa aagcggttag ctccttcggt cctccgatcg ttgtcagaag taagttggcc      7380
gcagtgttat cactcatggt tatggcagca ctgcataatt ctcttactgt catgccatcc      7440
gtaagatgct tttctgtgac tggtgagtac tcaaccaagt cattctgaga atagtgtatg      7500
cggcgaccga gttgctcttg cccggcgtca acacgggata ataccgcgcc acatagcaga      7560
actttaaaag tgctcatcat tggaaaacgt tcttcgggc gaaaactctc aaggatctta      7620
ccgctgttga gatccagttc gatgtaaccc actcgtgcac ccaactgatc ttcagcatct      7680
tttactttca ccagcgtttc tgggtgagca aaaacaggaa ggcaaaatgc cgcaaaaaag      7740
ggaataaggg cgacacggaa atgttgaata ctcatactct ccttttca atattattga      7800
agcatttatc agggttattg tctcatgagc ggatacatat ttgaatgtat ttagaaaaat      7860
aaacaaatag gggttccgcg cacatttccc cgaaaagtgc cacctgacgt ctaagaaacc      7920
attattatca tgacattaac ctataaaaat aggcgtatca cgaggccctt tcgtcttcaa      7980
```

<210> SEQ ID NO 3
<211> LENGTH: 7311
<212> TYPE: DNA
<213> ORGANISM: Artificial

<220> FEATURE:
<223> OTHER INFORMATION: Plasmid pLNMX

<400> SEQUENCE: 3

| | | | | | |
|---|---|---|---|---|---|
| gaattcatac | cagatcaccg | aaaactgtcc | tccaaatgtg | tccccctcac | actcccaaat | 60 |
| tcgcgggctt | ctgcctctta | gaccactcta | ccctattccc | cacactcacc | ggagccaaag | 120 |
| ccgcggccct | tccgtttctt | tgcttttgaa | agacccacc | cgtaggtggc | aagctagctt | 180 |
| aagtaacgcc | actttgcaag | gcatggaaaa | atacataact | gagaatagaa | aagttcagat | 240 |
| caaggtcagg | aacaaagaaa | cagctgaata | ccaaacagga | tatctgtggt | aagcggttcc | 300 |
| tgccccggct | cagggccaag | aacagatgag | acagctgagt | gatgggccaa | acaggatatc | 360 |
| tgtggtaagc | agttcctgcc | ccggctcggg | gccaagaaca | gatggtcccc | agatgcggtc | 420 |
| cagccctcag | cagtttctag | tgaatcatca | gatgtttcca | gggtgcccca | aggacctgaa | 480 |
| aatgaccctg | taccttattt | gaactaacca | atcagttcgc | ttctcgcttc | tgttcgcgcg | 540 |
| cttccgctct | ccgagctcaa | taaaagagcc | cacaacccct | cactcggcgc | gccagtcttc | 600 |
| cgatagactg | cgtcgcccgg | gtacccgtat | tcccaataaa | gcctcttgct | gtttgcatcc | 660 |
| gaatcgtggt | ctcgctgttc | cttgggaggg | tctcctctga | gtgattgact | acccacgacg | 720 |
| ggggtctttc | atttgggggc | tcgtccggga | tttggagacc | cctgcccagg | gaccaccgac | 780 |
| ccaccaccgg | gaggtaagct | ggccagcaac | ttatctgtgt | ctgtccgatt | gtctagtgtc | 840 |
| tatgtttgat | gttatgcgcc | tgcgtctgta | ctagttagct | aactagctct | gtatctggcg | 900 |
| gacccgtggt | ggaactgacg | agttctgaac | acccggccgc | aaccctggga | gacgtcccag | 960 |
| ggactttggg | ggccgttttt | gtggcccgac | ctgaggaagg | gagtcgatgt | ggaatccgac | 1020 |
| cccgtcagga | tatgtggttc | tggtaggaga | cgagaaccta | aaacagttcc | cgcctccgtc | 1080 |
| tgaattttg | ctttcggttt | ggaaccgaag | ccgcgcgtct | tgtctgctgc | agcgctgcag | 1140 |
| catcgttctg | tgttgtctct | gtctgactgt | gtttctgtat | ttgtctgaaa | attagggcca | 1200 |
| gactgttacc | actcccttaa | gtttgacctt | aggtcactgg | aaagatgtcg | agcggatcgc | 1260 |
| tcacaaccag | tcggtagatg | tcaagaagag | acgttgggtt | accttctgct | ctgcagaatg | 1320 |
| gccaaccttt | aacgtcggat | ggccgcgaga | cggcacctt | aaccgagacc | tcatcaccca | 1380 |
| ggttaagatc | aaggtctttt | cacctggccc | gcatggacac | ccagaccagg | tcccctacat | 1440 |
| cgtgacctgg | gaagcttgg | cttttgaccc | cctccctgg | gtcaagccct | tgtacaccc | 1500 |
| taagcctccg | cctcctcttc | ctccatccgc | cccgtctctc | cccttgaac | ctcctcgttc | 1560 |
| gaccccgcct | cgatcctccc | tttatccagc | cctcactcct | tctctaggcg | ccggaattcc | 1620 |
| gatctgatca | agagacagga | tgaggatcgt | ttcgcatgat | tgaacaagat | ggattgcacg | 1680 |
| caggttctcc | ggccgcttgg | gtggagaggc | tattcggcta | tgactgggca | caacagacaa | 1740 |
| tcggctgctc | tgatgccgcc | gtgttccggc | tgtcagcgca | ggggcgcccg | gttctttttg | 1800 |
| tcaagaccga | cctgtccggt | gccctgaatg | aactgcagga | cgaggcagcg | cggctatcgt | 1860 |
| ggctggccac | gacgggcgtt | ccttgcgcag | ctgtgctcga | cgttgtcact | gaagcgggaa | 1920 |
| gggactggct | gctattgggc | gaagtgccgg | ggcaggatct | cctgtcatct | caccttgctc | 1980 |
| ctgccgagaa | agtatccatc | atggctgatg | caatgcggcg | gctgcatacg | cttgatccgg | 2040 |
| ctacctgccc | attcgaccac | caagcgaaac | atcgcatcga | gcgagcacgt | actcggatgg | 2100 |
| aagccggtct | tgtcgatcag | gatgatctgg | acgaagagca | tcaggggctc | gcgccagccg | 2160 |
| aactgttcgc | caggctcaag | gcgcgcatgc | ccgacggcga | ggatctcgtc | gtgacccatg | 2220 |

```
gcgatgcctg cttgccgaat atcatggtgg aaaatggccg ctttttctgga ttcatcgact   2280 gtggccggct gggtgtggcg gaccgctatc aggacatagc gttggctacc cgtgatattg   2340
ctgaagagct tggcggcgaa tgggctgacc gcttcctcgt gctttacggt atcgccgctc   2400
ccgattcgca gcgcatcgcc ttctatcgcc ttcttgacga gttcttctga gcgggactct   2460
ggggttcgaa atgaccgacc aagcgacgcc caacctgcca tcacgagatt tcgattccac   2520
cgccgccttc tatgaaaggt tgggcttcgg aatcgttttc cgggacgccg gctggatgat   2580
cctccagcgc ggggatctca tgctggagtt cttcgcccac cccgggctcg atccctcgc    2640 gagttggttc agctgctgcc tgaggctgga cgacctcgcg gagttctacc ggcagtgcaa   2700
atccgtcggc atccaggaaa ccagcagcgg ctatccgcgc atccatgccc ccgaactgca   2760
ggagtgggga ggcacgatgg ccgctttggt cgaggcggat ccgggcagaa atggttgaac   2820
tcccgagagt gtcctacacc taggggagaa gcagccaagg ggttgtttcc caccaaggac   2880
gacccgtctg cgcacaaacg gatgagccca tcagacaaag acatattcat tctctgctgc   2940
aaacttggca tagctctgct ttgcctgggg ctattggggg aagttgcggt tcgtgctcgc   3000
agggctctca cccttgactc ttttaatagc tcttctgtgc aagattacaa tctaaacaat   3060
tcggagaact cgaccttcct cctgaggcaa ggaccacagc caacttcctc ttacaagccg   3120
catcgatttt gtccttcaga aatagaaata agaatgcttg ctaaaaatta tatttttacc   3180
aataagacca atccaatagg tagattatta gttactatgt taagaaatga atcattatct   3240
tttagtacta tttttactca aattcagaag ttagaaatgg gaatagaaaa tagaaagaga   3300
cgctcaacct caattgaaga acaggtgcaa ggactattga ccacaggcct agaagtaaaa   3360
aagggaaaaa agagtgtttt tgtcaaaata ggagacaggg ggtggcaacc agggacttat   3420
aggggacctt acatctacag accaacagat gccccttac catatacagg aagatatgac    3480
ttaaattggg ataggtgggt tacagtcaat ggctataaag tgttatatag atccctccct   3540
tttcgtgaaa gactcgccag agctagacct ccttggtgta tgttgtctca agaagaaaaa   3600
gacgacatga aacaacaggt acatgattat atttatctag gaacaggaat gcacttttgg   3660
ggaaagattt tccataccaa ggaggggaca gtggctggac taatagaaca ttattctgca   3720
aaaactcatg gcatgagtta ttatgaatag ccttttattgg cccaaccttg cggttcccag   3780
ggcttaagta agttttttggt tacaaactgt tcttaaaacg aggatgtgag acaagtggtt   3840
tcctgacttg gtttggtatc aaaggttctg atctgagctc tgagtgttct attttcctat   3900 gttctttttgg aatttatcca atcttatgt aaatgcttat gtaaaccaag atataaaga    3960 gtgctgatttt tttgagtaaa cttgcaacag tcctaacatt cacctcttgt gtgtttgtgt   4020
ctgttcgcca tcccgtctcc gctcgtcact tatccttcac tttccagagg gtcccccgc    4080 agaccccggc gaccctcagg tcggccgact gcggcagctg gcgcccgaac agggaccctc   4140
ggataagtga cccttgtctc tatttctact atttggtgtt tgtcttgtat tgtctctttc   4200
ttgtctggct atcatcacaa gagcggaacg gactcaccat agggaccaag cttgtcgaca   4260
tttctgcaga tatccatcac actggcggcc gctcgagcat gcatctagaa catcgataaa   4320 ataaagatt ttatttagtc tccagaaaaa gggggggaatg aaagacccca cctgtaggtt   4380
tggcaagcta gcttaagtaa cgccattttg caaggcatgg aaaaatacat aactgagaat   4440
agagaagttc agatcaaggt caggaacaga tggaacagct gaatatgggc caaacaggat   4500
atctgtggta agcagttcct gccccggctc agggccaaga acagatggaa cagctgaata   4560
tgggccaaac aggatatctg tggtaagcag ttcctgcccc ggctcagggc caagaacaga   4620
```

-continued

```
tggtcccag atgcggtcca gccctcagca gtttctagag aaccatcaga tgtttccagg    4680
gtgcccaag gacctgaaat gaccctgtgc cttatttgaa ctaaccaatc agttcgcttc    4740
tcgcttctgt tcgcgcgctt ctgctccccg agctcaataa aagagcccac aacccctcac   4800
tcggggcgcc agtcctccga ttgactgagt cgcccgggta cccgtgtatc caataaaccc   4860
tcttgcagtt gcatccgact tgtggtctcg ctgttccttg ggagggtctc ctctgagtga   4920
ttgactaccc gtcagcgggg gtcttttcatt tgggggctcg tccgggatcg ggagacccct  4980
gcccagggac caccgaccca ccaccgggag gtaagctggc tgcctcgcgc gtttcggtga   5040
tgacggtgaa aacctctgac acatgcagct cccggagacg gtcacagctt gtctgtaagc   5100
ggatgccggg agcagacaag cccgtcaggg cgcgtcagcg ggtgttggcg ggtgtcgggg   5160
cgcagccatg acccagtcac gtagcgatag cggagtgtat actggcttaa ctatgcggca   5220
tcagagcaga ttgtactgag agtgcaccat atgcggtgtg aaataccgca cagatgcgta   5280
aggagaaaat accgcatcag gcgctcttcc gcttcctcgc tcactgactc gctgcgctcg   5340
gtcgttcggc tgcggcgagc ggtatcagct cactcaaagg cggtaatacg gttatccaca   5400
gaatcagggg ataacgcagg aaagaacatg tgagcaaaag gccagcaaaa ggccaggaac   5460
cgtaaaaagg ccgcgttgct ggcgtttttc cataggctcc gccccctga cgagcatcac    5520
aaaaatcgac gctcaagtca gaggtggcga acccgacag gactataaag ataccaggcg   5580
tttcccctg gaagctccct cgtgcgctct cctgttccga ccctgccgct taccggatac    5640
ctgtccgcct ttctcccttc gggaagcgtg gcgctttctc atagctcacg ctgtaggtat   5700
ctcagttcgg tgtaggtcgt tcgctccaag ctgggctgtg tgcacgaacc cccgttcag    5760
cccgaccgct gcgccttatc cggtaactat cgtcttgagt ccaacccggt aagacacgac   5820
ttatcgccac tggcagcagc cactggtaac aggattagca gagcgaggta tgtaggcggt   5880
gctacagagt tcttgaagtg gtggcctaac tacggctaca ctagaaggac agtatttggt   5940
atctgcgctc tgctgaagcc agttaccttc ggaaaaagag ttggtagctc ttgatccggc   6000
aaacaaacca ccgctggtag cggtggtttt tttgtttgca agcagcagat tacgcgcaga   6060
aaaaaaggat ctcaagaaga tcctttgatc ttttctacgg ggtctgacgc tcagtggaac   6120
gaaaactcac gttaagggat tttggtcatg agattatcaa aaaggatctt cacctagatc   6180
cttttaaatt aaaaatgaag ttttaaatca atctaaagta tatatgagta aacttggtct   6240
gacagttacc aatgcttaat cagtgaggca cctatctcag cgatctgtct atttcgttca   6300
tccatagttg cctgactccc cgtcgtgtag ataactacga tacgggaggg cttaccatct   6360
ggccccagtg ctgcaatgat accgcgagac ccacgctcac cggctccaga tttatcagca   6420
ataaaccagc cagccggaag ggccgagcgc agaagtggtc ctgcaacttt atccgcctcc   6480
atccagtcta ttaattgttg ccgggaagct agagtaagta gttcgccagt taatagtttg   6540
cgcaacgttg ttgccattgc tgcaggcatc gtggtgtcac gctcgtcgtt tggtatggct   6600
tcattcagct ccggttccca acgatcaagg cgagttacat gatcccccat gttgtgcaaa   6660
aaagcggtta gctccttcgg tcctccgatc gttgtcagaa gtaagttggc cgcagtgtta   6720
tcactcatgg ttatggcagc actgcataat tctcttactg tcatgccatc cgtaagatgc   6780
ttttctgtga ctggtgagta ctcaaccaag tcattctgag aatagtgtat gcggcgaccg   6840
agttgctctt gcccggcgtc aacacgggat aataccgcgc cacatagcag aactttaaaa   6900
gtgctcatca ttggaaaacg ttcttcgggg cgaaaactct caaggatctt accgctgttg   6960
```

-continued

| | |
|---|---|
| agatccagtt cgatgtaacc cactcgtgca cccaactgat cttcagcatc ttttactttc | 7020 |
| accagcgttt ctgggtgagc aaaaacagga aggcaaaatg ccgcaaaaaa gggaataagg | 7080 |
| gcgacacgga aatgttgaat actcatactc ttccttttc aatattattg aagcatttat | 7140 |
| cagggttatt gtctcatgag cggatacata tttgaatgta tttagaaaaa taaacaaata | 7200 |
| ggggttccgc gcacatttcc ccgaaaagtg ccacctgacg tctaagaaac cattattatc | 7260 |
| atgacattaa cctataaaaa taggcgtatc acgaggccct ttcgtcttca a | 7311 |

<210> SEQ ID NO 4
<211> LENGTH: 7885
<212> TYPE: DNA
<213> ORGANISM: Artificial
<220> FEATURE:
<223> OTHER INFORMATION: Plasmid pLNMi2X

<400> SEQUENCE: 4

| | |
|---|---|
| gaattcatac cagatcaccg aaaactgtcc tccaaatgtg tcccctcac actcccaaat | 60 |
| tcgcgggctt ctgcctctta gaccactcta ccctattccc cacactcacc ggagccaaag | 120 |
| ccgcggccct tccgtttctt tgcttttgaa agacccacc cgtaggtggc aagctagctt | 180 |
| aagtaacgcc actttgcaag gcatggaaaa atacataact gagaatagaa aagttcagat | 240 |
| caaggtcagg aacaaagaaa cagctgaata ccaaacagga tatctgtggt aagcggttcc | 300 |
| tgccccggct cagggccaag aacagatgag acagctgagt gatgggccaa acaggatatc | 360 |
| tgtggtaagc agttcctgcc ccggctcggg gccaagaaca gatggtcccc agatgcggtc | 420 |
| cagccctcag cagtttctag tgaatcatca gatgtttcca gggtgcccca aggacctgaa | 480 |
| aatgaccctg taccttattt gaactaacca atcagttcgc ttctcgcttc tgttcgcgcg | 540 |
| cttccgctct ccgagctcaa taaaagagcc cacaacccct cactcggcgc gccagtcttc | 600 |
| cgatagactg cgtcgcccgg gtacccgtat tcccaataaa gcctcttgct gtttgcatcc | 660 |
| gaatcgtggt ctcgctgttc cttgggaggg tctcctctga gtgattgact acccacgacg | 720 |
| ggggtctttc atttggggc tcgtccggga tttggagacc cctgcccagg gaccaccgac | 780 |
| ccaccaccgg gaggtaagct ggccagcaac ttatctgtgt ctgtccgatt gtctagtgtc | 840 |
| tatgtttgat gttatgcgcc tgcgtctgta ctagttagct aactagctct gtatctggcg | 900 |
| gacccgtggt ggaactgacg agttctgaac accggccgc aaccctggga cgtcccag | 960 |
| ggactttggg ggccgttttt gtggcccgac ctgaggaagg gagtcgatgt ggaatccgac | 1020 |
| cccgtcagga tatgtggttc tggtaggaga cgagaaccta aaacagttcc cgcctccgtc | 1080 |
| tgaatttttg cttcggttt ggaaccgaag ccgcgcgtct tgtctgctgc agcgctgcag | 1140 |
| catcgttctg tgttgtctct gtctgactgt gtttctgtat ttgtctgaaa attagggcca | 1200 |
| gactgttacc actcccttaa gtttgacctt aggtcactgg aaagatgtcg agcggatcgc | 1260 |
| tcacaaccag tcggtagatg tcaagaagag acgttgggtt accttctgct ctgcagaatg | 1320 |
| gccaaccttt aacgtcggat ggccgcgaga cggcaccttt aaccgagacc tcatcaccca | 1380 |
| ggttaagatc aaggtcttt cacctggccc gcatggacac ccagaccagg tccctacat | 1440 |
| cgtgacctgg gaagcttgg cttttgaccc cctccctgg gtcaagccct ttgtacaccc | 1500 |
| taagcctccg cctcctcttc ctccatccgc cccgtctctc cccttgaac ctcctcgttc | 1560 |
| gaccccgcct cgatcctccc tttatccagc cctcactcct tctctaggcg ccggaattcc | 1620 |
| gatctgatca agagacagga tgaggatcgt ttcgcatgat tgaacaagat ggattgcacg | 1680 |
| caggttctcc ggccgcttgg gtggagaggc tattcggcta tgactgggca caacagacaa | 1740 |

```
tcggctgctc tgatgccgcc gtgttccggc tgtcagcgca ggggcgcccg gttcttttg    1800 tcaagaccga cctgtccggt gccctgaatg aactgcagga cgaggcagcg cggctatcgt    1860
ggctggccac gacgggcgtt ccttgcgcag ctgtgctcga cgttgtcact gaagcgggaa    1920
gggactggct gctattgggc gaagtgccgg ggcaggatct cctgtcatct caccttgctc    1980
ctgccgagaa agtatccatc atggctgatg caatgcggcg gctgcatacg cttgatccgg    2040
ctacctgccc attcgaccac caagcgaaac atcgcatcga gcgagcacgt actcggatgg    2100
aagccggtct tgtcgatcag gatgatctgg acgaagagca tcaggggctc gcgccagccg    2160
aactgttcgc caggctcaag gcgcgcatgc ccgacggcga ggatctcgtc gtgacccatg    2220
gcgatgcctg cttgccgaat atcatggtgg aaaatggccg cttttctgga ttcatcgact    2280
gtggccggct gggtgtggcg gaccgctatc aggacatagc gttggctacc cgtgatattg    2340
ctgaagagct tggcggcgaa tgggctgacc gcttcctcgt gctttacggt atcgccgctc    2400
ccgattcgca gcgcatcgcc ttctatcgcc ttcttgacga gttcttctga gcgggactct    2460
ggggttcgaa atgaccgacc aagcgacgcc caacctgcca tcacgagatt tcgattccac    2520
cgccgccttc tatgaaaggt tgggcttcgg aatcgttttc cgggacgccg gctggatgat    2580
cctccagcgc gggatctca tgctggagtt cttcgcccac cccgggctcg atccctcgc     2640 gagttggttc agctgctgcc tgaggctgga cgacctcgcg gagttctacc ggcagtgcaa    2700
atccgtcgga atccaggaaa ccagcagcgg ctatccgcgc atccatgccc cgaactgca    2760 ggagtgggga ggcacgatgg ccgctttggt cgaggcggat ccgggcagaa atggttgaac    2820
tcccgagagt gtcctacacc tagggagaa gcagccaagg ggttgtttcc caccaaggac    2880
gacccgtctg cgcacaaacg gatgagccca tcagacaaag acatattcat tctctgctgc    2940
aaacttggca tagctctgct ttgcctgggg ctattggggg aagttgcggt tcgtgctcgc    3000
agggctctca cccttgactc ttttaatagc tcttctgtgc aagattacaa tctaaacaat    3060
tcggagaact cgaccttcct cctgaggcaa ggaccacagc caacttcctc ttacaagccg    3120
catcgatttt gtccttcaga aatagaaata agaatgcttg ctaaaaatta tattttacc    3180 aataagacca atccaatagg tagattatta gttactatgt taagaaatga atcattatct    3240
tttagtacta ttttttactca aattcagaag ttagaaatgg gaatagaaaa tagaaagaga    3300
cgctcaacct caattgaaga acaggtgcaa ggactattga ccacaggcct agaagtaaaa    3360
aagggaaaaa agagtgtttt tgtcaaaata ggagacaggt ggtggcaacc agggacttat    3420 agggacctt acatctacag accaacagat gccccttac catatacagg aagatatgac     3480
ttaaattggg ataggtgggt tacagtcaat ggctataaag tgttatatag atccctccct    3540
tttcgtgaaa gactcgccag agctagacct ccttggtgta tgttgtctca agaagaaaaa    3600
gacgacatga acaacaggt acatgattat atttatctag gaacaggaat gcacttttgg    3660
ggaaagattt tccataccaa ggagggaca gtggctggac taatagaaca ttattctgca     3720
aaaactcatg gcatgagtta ttatgaatag ccttttattgg cccaacctg cggttcccag    3780 ggcttaagta agttttggt tacaaactgt tcttaaaacg aggatgtgag acaagtggtt     3840
tcctgacttg gtttggtatc aaaggttctg atctgagctc tgagtgttct attttcctat    3900
gttcttttgg aattatcca atcttatgt aaatgcttat gtaaaccaag atataaaga      3960 gtgctgattt tttgagtaaa cttgcaacag tcctaacatt cacctcttgt gtgtttgtgt    4020
ctgttcgcca tcccgtctcc gctcgtcact tatccttcac ttttccagagg gtccccccgc    4080
```

-continued

| | | | | | |
|---|---|---|---|---|---|
| agacccggc | gaccctcagg | tcggccgact | gcggcagctg | gcgcccgaac | agggaccctc | 4140 |
| ggataagtga | cccttgtctc | tatttctact | atttggtgtt | tgtcttgtat | tgtctctttc | 4200 |
| ttgtctggct | atcatcacaa | gagcggaacg | gactcaccat | agggaccaag | cttgtcgaca | 4260 |
| tctagggcgg | ccaattccgc | ccctctccct | ccccccccc | taacgttact | ggccgaagcc | 4320 |
| gcttggaata | aggccggtgt | gcgtttgtct | atatgtgatt | ttccaccata | ttgccgtctt | 4380 |
| ttggcaatgt | gagggcccgg | aaacctggcc | ctgtcttctt | gacgagcatt | cctagggtc | 4440 |
| tttcccctct | cgccaaagga | atgcaaggtc | tgttgaatgt | cgtgaaggaa | gcagttcctc | 4500 |
| tggaagcttc | ttgaagacaa | acaacgtctg | tagcgaccct | ttgcaggcag | cggaaccccc | 4560 |
| cacctggcga | caggtgcctc | tgcggccaaa | agccacgtgt | ataagataca | cctgcaaagg | 4620 |
| cggcacaacc | ccagtgccac | gttgtgagtt | ggatagttgt | ggaaagagtc | aaatggctct | 4680 |
| cctcaagcgt | attcaacaag | gggctgaagg | atgcccagaa | ggtaccccat | tgtatgggat | 4740 |
| ctgatctggg | gcctcggtgc | acatgcttta | catgtgttta | gtcgaggtta | aaaaacgtc | 4800 |
| taggccccc | gaaccacggg | gacgtggttt | tcctttgaaa | aacacgccaa | taatatgggc | 4860 |
| ggccgctcga | gcatgcatct | agaacatcga | taaaataaaa | gatttatttt | agtctccaga | 4920 |
| aaaagggggg | aatgaaagac | cccacctgta | ggtttggcaa | gctagcttaa | gtaacgccat | 4980 |
| tttgcaaggc | atggaaaaat | acataactga | gaatagagaa | gttcagatca | aggtcaggaa | 5040 |
| cagatggaac | agctgaatat | gggccaaaca | ggatatctgt | ggtaagcagt | tcctgccccg | 5100 |
| gctcagggcc | aagaacagat | ggaacagctg | aatatgggcc | aaacaggata | tctgtggtaa | 5160 |
| gcagttcctg | ccccggctca | gggccaagaa | cagatggtcc | ccagatgcgg | tccagccctc | 5220 |
| agcagtttct | agagaaccat | cagatgtttc | cagggtgccc | caaggacctg | aaatgaccct | 5280 |
| gtgccttatt | tgaactaacc | aatcagttcg | cttctcgctt | ctgttcgcgc | gcttctgctc | 5340 |
| cccgagctca | ataaaagagc | ccacaacccc | tcactcgggg | cgccagtcct | ccgattgact | 5400 |
| gagtcgcccg | ggtacccgtg | tatccaataa | accctcttgc | agttgcatcc | gacttgtggt | 5460 |
| ctcgctgttc | cttgggaggg | tctcctctga | gtgattgact | accgtcagc | ggggtctttt | 5520 |
| catttggggg | ctcgtccggg | atcggagac | ccctgcccag | ggaccaccga | cccaccaccg | 5580 |
| ggaggtaagc | tggctgcctc | gcgcgtttcg | gtgatgacgt | tgaaaacctc | tgacacatgc | 5640 |
| agctcccgga | gacggtcaca | gcttgtctgt | aagcggatgc | cgggagcaga | caagcccgtc | 5700 |
| agggcgcgtc | agcgggtgtt | ggcgggtgtc | ggggcgcagc | catgacccag | tcacgtagcg | 5760 |
| atagcggagt | gtatactggc | ttaactatgc | ggcatcagag | cagattgtac | tgagagtgca | 5820 |
| ccatatgcgg | tgtgaaatac | cgcacagatg | cgtaaggaga | aaataccgca | tcaggcgctc | 5880 |
| ttccgcttcc | tcgctcactg | actcgctgcg | ctcggtcgtt | cggctgcggc | gagcggtatc | 5940 |
| agctcactca | aaggcggtaa | tacggttatc | cacagaatca | gggataacg | caggaaagaa | 6000 |
| catgtgagca | aaaggccagc | aaaaggccag | gaaccgtaaa | aaggccgcgt | tgctggcgtt | 6060 |
| tttccatagg | ctccgccccc | ctgacgagca | tcacaaaaat | cgacgctcaa | gtcagaggtg | 6120 |
| gcgaaacccg | acaggactat | aaagatacca | ggcgtttccc | cctggaagct | ccctcgtgcg | 6180 |
| ctctcctgtt | ccgaccctgc | cgcttaccgg | atacctgtcc | gcctttctcc | cttcgggaag | 6240 |
| cgtggcgctt | tctcatagct | cacgctgtag | gtatctcagt | tcggtgtagg | tcgttcgctc | 6300 |
| caagctgggc | tgtgtgcacg | aaccccccgt | tcagcccgac | cgctgcgcct | tatccggtaa | 6360 |
| ctatcgtctt | gagtccaacc | cggtaagaca | cgacttatcg | ccactggcag | cagccactgg | 6420 |
| taacaggatt | agcagagcga | ggtatgtagg | cggtgctaca | gagttcttga | agtggtggcc | 6480 |

```
taactacggc tacactagaa ggacagtatt tggtatctgc gctctgctga agccagttac    6540
cttcggaaaa agagttggta gctcttgatc cggcaaacaa accaccgctg gtagcggtgg    6600 ttttttttgtt tgcaagcagc agattacgcg cagaaaaaaa ggatctcaag aagatcctttt   6660 gatctttttct acggggtctg acgctcagtg gaacgaaaac tcacgttaag ggattttggt    6720
catgagatta tcaaaaagga tcttcaccta gatcctttta aattaaaaat gaagttttaa    6780
atcaatctaa agtatatatg agtaaacttg gtctgacagt taccaatgct taatcagtga    6840
ggcacctatc tcagcgatct gtctatttcg ttcatccata gttgcctgac tccccgtcgt    6900
gtagataact acgatacggg agggcttacc atctggcccc agtgctgcaa tgataccgcg    6960
agacccacgc tcaccggctc cagatttatc agcaataaac cagccagccg gaagggccga    7020
gcgcagaagt ggtcctgcaa ctttatccgc ctccatccag tctattaatt gttgccggga    7080
agctagagta agtagttcgc cagttaatag tttgcgcaac gttgttgcca ttgctgcagg    7140
catcgtggtg tcacgctcgt cgtttggtat ggcttcattc agctccggtt cccaacgatc    7200
aaggcgagtt acatgatccc ccatgttgtg caaaaaagcg gttagctcct tcggtcctcc    7260
gatcgttgtc agaagtaagt tggccgcagt gttatcactc atggttatgg cagcactgca    7320
taattctctt actgtcatgc catccgtaag atgcttttct gtgactggtg agtactcaac    7380
caagtcattc tgagaatagt gtatgcggcg accgagttgc tcttgcccgg cgtcaacacg    7440
ggataatacc gcgccacata gcagaacttt aaaagtgctc atcattggaa aacgttcttc    7500
ggggcgaaaa ctctcaagga tcttaccgct gttgagatcc agttcgatgt aacccactcg    7560
tgcacccaac tgatcttcag catcttttac tttcaccagc gtttctgggt gagcaaaaac    7620
aggaaggcaa aatgccgcaa aaaagggaat aagggcgaca cggaaatgtt gaatactcat    7680
actcttcctt tttcaatatt attgaagcat ttatcagggt tattgtctca tgagcggata    7740
catatttgaa tgtatttaga aaaataaaca aataggggtt ccgcgcacat ttccccgaaa    7800
agtgccacct gacgtctaag aaaccattat tatcatgaca ttaacctata aaaataggcg    7860
tatcacgagg ccctttcgtc ttcaa                                          7885
```

TRANS-SOMATICS WITH GENE TRANSFER INTO MAMMARY EPITHELIAL CELLS

This application is a continuation of International Application Serial No. PCT/CA98/00607, filed Jun. 25, 1998, which claims priority to Canadian Application No. 2,224,108, filed Feb. 24, 1998.

FIELD OF INVENTION

The present invention relates to a method of producing value-added milk by the incorporation of specific DNA sequence(s) into the cells of the mammary gland. The term "value-added milk" is meant to mean milk containing a valuable compound, such as a pharmaceutical, as well as milk with a changed composition so that the market value of the milk is enhanced.

BACKGROUND OF THE INVENTION

This invention is based upon a technique to transfer a gene, and related non-translated control sequences, into the secretory cells of the mammary gland to produce new compounds in milk and/or to alter the milk composition.

An example of a compound produced into milk by this method would be a pharmaceutical which cannot be manufactured in a biologically active state. This invention provides an alternative method of producing such pharmaceuticals into milk using the synthetic capabilities of the mammary epithelial cell.

Mammals produce copious amounts of complex proteins into milk to provide nutrition for their young. To harness this capability, the DNA of, for example a valuable pharmaceutical, can be inserted into a mammary epithelial cell and this cell then will produce the active, pharmaceutical compound into the secreted milk. In a cow, the udder will act as a receptacle to hold the milk until it can be collected. The milk containing the added compound can be processed to extract and purify this pharmaceutical compound for subsequent sale, possibly to the medical and/or veterinary communities, or the milk could be consumed directly as a therapeutic agent.

At present there are two basic techniques that can be used to produce value-added milk. The first is to create a transgenic animal by microinjection or transfection of foreign DNA into an ovum or a fertilized egg. Incorporation of DNA at this stage in development generally results in a transgenic animal which carries the inserted DNA in every cell.

There are positive and negative aspects of producing a transgenic animal which expresses foreign proteins in its milk. A positive point is that a single founder animal can create a population of transgenic animals by natural reproduction. However, progenies do not always produce the exogenous protein at the same level as the original animal. Negative aspects include the technically difficult procedures required to produce the animal and the long time between adding the foreign DNA and harvesting the exogenous protein. In addition, the presence of even very small amounts of an active pharmaceutical in every tissue may be detrimental to the health of the animal.

An alternative method is to produce value-added milk by adding the desired DNA only to the cells of the mammary gland of the animal. This results in a trans-somatic animal (or chimera) which contains the inserted DNA essentially in only one tissue, the mammary gland.

Trans-somatic animals have the advantage that they can be produced with less technical difficulty. They also can be produced quickly so that there is a period of only weeks to months between adding the foreign DNA and harvesting the exogenous protein. Moreover, since only one tissue contains the added DNA and produces the resulting compound, health risks to the trans-somatic animal are reduced. Although the DNA is not passed on to the progeny, this is compensated for by the ease and speed with which a trans-somatic animal can be produced.

A trans-somatic goat which expresses human growth hormone (hGH) into milk has been produced by Archer et al. (1994). In Archer the viral-derived particles were infused into the mammary gland for approximately every two days for two weeks. The levels of the compound, human growth hormone, which was used as an example, were very low and approached background levels after the first day. Also Gould et al. (U.S. Pat. No. 5,215,904) described a method for increasing the rate of mitosis of mammary epithelial cells and then exposing these cells to viral particles for integration of the desired DNA into the epithelial cell.

To produce either a trans-somatic or a transgenic animal, exogenous DNA must pass through the exterior cell membrane. Eukaryotic cells have evolved a membrane which is impervious to most substances including heterologous DNA. Numerous techniques have been developed to bypass this barrier. These include:

electroporation, carrier lipids (liposomes, negative, positive or neutral charged vesicles), mechanical wounding of cells including microinjection, liquid or air-jet pressure and scrape loading, use of particles composed partially or wholly of viral proteins.

Methods which have successfully produced trans-somatic animals include:

1) Arterial injection of DNA carried in liposomes (small lipid vesicles) was used to produce a trans-somatic mouse (Thierry et al. 1995). This technique can be adapted to deliver DNA to the mammary gland by injection into the major artery serving the mammary gland but circulation of the blood carrying the DNA can result in transfection of multiple tissues.

2) Direct injection of the DNA into tissues was used successfully to add foreign DNA to muscle and other tissues (Furth et al. 1992). This technique can be adapted to inject virus-like particles, carrying the foreign DNA, directly into the tissue of the udder.

3) Use of viral-derived particles carrying DNA coding for human growth hormone (hGH) were infused through the teat canal, for example by Archer et al. (1994). This resulted in production of trans-somatic goats which expressed hGH into the milk.

Viruses reproduce within cells and therefore have evolved a technique to by-pass the protective cell membrane to deliver the viral genome (DNA) into a host cell. To enter a cell, protein(s) of the outer viral shells first bind to receptors on the cell surface and then the virus is internalized.

The method used by Archer involves transfecting a cell line with DNA coding for various, but not all, proteins of a virus. This cell line, called a "packaging cell line", will produce empty virus shells which can bind to receptors on the host cell membrane. When heterologous DNA, coding for a pharmaceutical or other milk modification, is transfected into the packaging cell line, this DNA will be packaged into the viral-derived particle. When the viral-derived particle comes in contact with a milk-producing cell, the viral proteins of the shell ensure that the heterologous DNA is carried into the cell. Other viral proteins, associated with the particle, integrate the heterologous DNA into the genome of the host cell so that the protein encoded by the DNA can be expressed. In this method the viral-derived particles are used to introduce the heterologous DNA into the mammary gland.

The trans-somatic methods of the prior art offer advantages over the transgenic method; however the very low levels of foreign protein in the milk of the trans-somatic animal have limited the commercial success of these methods.

Thus the present invention is directed to methods of improving the yield of the foreign protein in the milk of a trans-somatic animal.

SUMMARY OF THE INVENTION

The present invention relates to a method of producing valuable compounds into milk and/or changing the composition of milk so as to enhance its properties and/or its marketability. More specifically the present invention relates to the addition of specific DNA sequences, including non-translated regulatory sequences, to the cells of the mammary gland and the subsequent expression of compound(s) encoded by that DNA into the milk. Other DNA sequences that enhance the efficiency of production of the compound, enhance the stability of the compound, or result in biological activity of the compound can also be added to the mammary epithelial cells either at the same time or at a different time.

The novel method of the present invention involves the use of viral-derived particles and packaging cells which produce these particles for infusion into the mammary gland through the teat canal. The packaging cells will attach and survive for a period of time within the mammary gland. While the cells are viable, they will supply a continuous source of viral-derived particles. These viral-derived particles trans-infect only dividing cells and are destroyed relatively quickly in the mammary gland. Thus a continuous supply of viral-derived particles from the packaging cells present in the mammary gland will ensure that viral-derived particles are present and can trans-infect the mammary epithelial cells whenever they divide.

The packaging cells and viral-derived particles can be from retroviruses and from non-retroviruses. Most retroviral-derived particles trans-infect only dividing cells. Non-retroviral particles such as those from adenovirus, Epstein-Barr virus, or other viruses trans-infect non-dividing cells. Thus a mixture of the two types of particles, and the associated packaging cells if needed, will ensure delivery of the packaged DNA to the maximum number of cells. Moreover, DNA can be packaged into viral-derived particles in vitro and these can be used for trans-infection as well.

This method can be used alone or in combination with other novel methods designed to ensure that the viral-derived particles are correctly positioned to trans-infect the mammary epithelial cells. Increasing the trans-infection of the mammary epithelial cells with the viral particles will result in a higher concentration of the valuable compound in the milk along with possible other compounds produced from the inserted DNA that will enhance the efficient production, stability or activity of the compound.

Thus according to the present invention there is provided a method of producing a trans-somatic mammal, wherein said method provides the incorporation of a DNA sequence into the secretory cells of the mammary gland to alter the composition of the milk, comprising the steps of: providing a vector containing a DNA sequence encoding a valuable compound; packaging said vector into a cell line; preparing a solution comprising the packaged vector and cell line producing said packaged vector; and delivering said solution into the mammary gland to allow the incorporation of the DNA into the secretory cells of the mammary gland.

BRIEF DESCRIPTION OF THE DRAWINGS

These and other features of the invention will become more apparent from the following description in which reference is made to the appended drawings wherein.

DESCRIPTION OF THE PREFERRED EMBODIMENT

Figure 1:
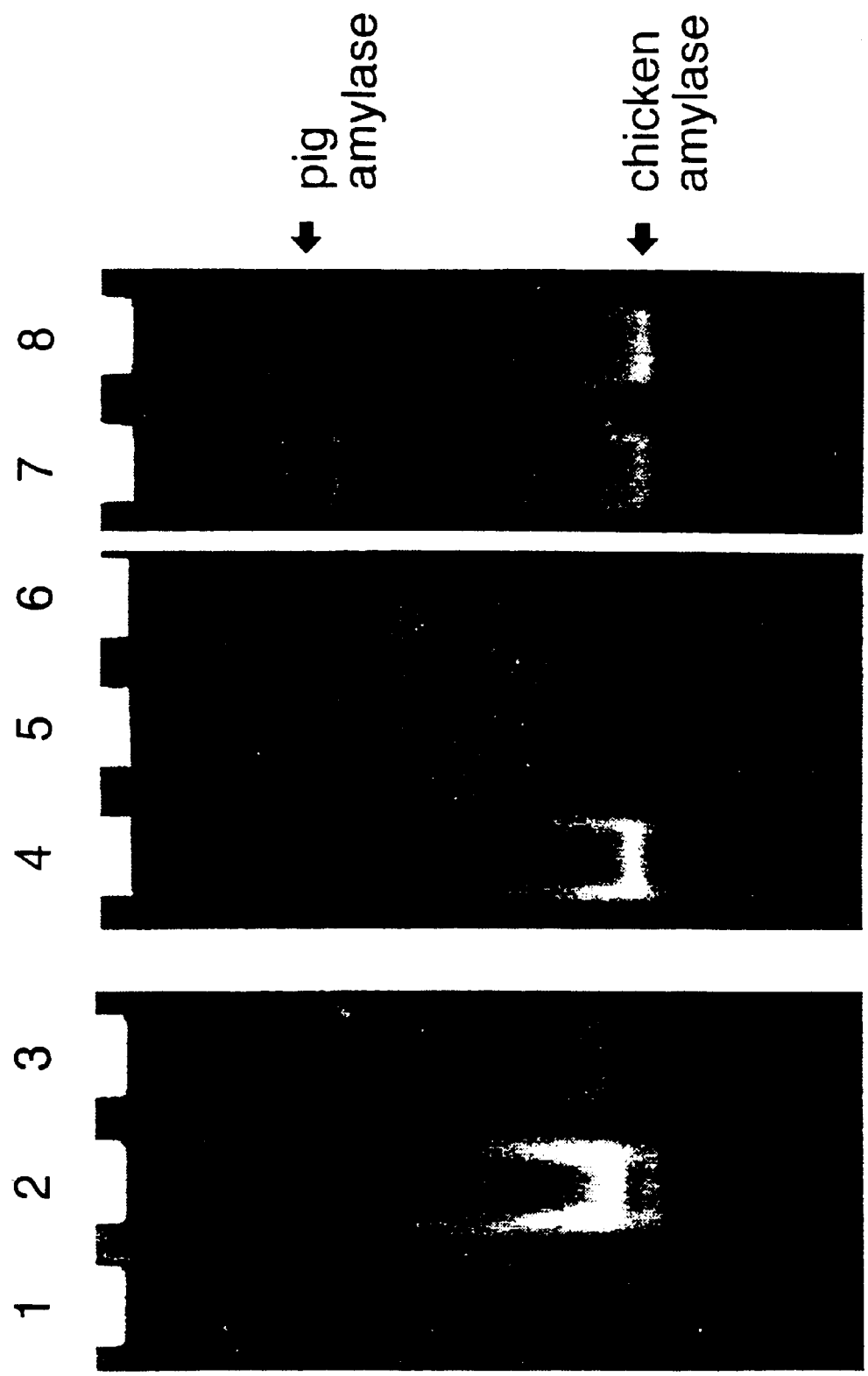
FIG. 1 shows the presence of amylase in an udder infused with Clone 10 (left hind quarter) and Clone 12 (right hind quarter). The left front quarter was left untouched as a negative control and the right front quarter was infused with DMEM and Polybrene but no cells, to serve as a further negative control. Lanes 1, 2 & 3, early premilk from 3 quarters of cow #99. Lane 1, control quarter (RF−); Lane 2, treated quarter (RH+); Lane 3, treated quarter (LH+). Lanes 4, 5 & 6, late premilk from cow #99. Lane 4, treated quarter (LH+); Lane 5, treated quarter (RH+); Lane 6, control quarter (RH−). Lane 7, mixture of pig and chicken amylase standards; Lane 8, chicken amylase standard.

The present invention relates to a method to transfer a gene or genes, and related non-translated control sequences into the secretory cells of a mammary gland to produce "value-added milk". The term "value-added milk" is meant to mean milk containing a valuable compound, such as a pharmaceutical, as well as milk with a changed composition so that the market value of the milk is enhanced.

Pharmaceuticals according to the present invention can include, but are not limited to: a tissue plasminogen activator, a blood clotting factor, an antibody, a protein to aid in weight reduction, a galactosyltransferase, a growth factor, an oncoprotein, a protease inhibitor, a hormone, a milk protein, a hormone receptor, a tumor suppressor protein, an aging inhibitor, or an erythropoietin.

According to the present invention there is provided a suitable DNA vector (plasmid) containing the desired DNA sequence encoding the heterologous protein (valuable compound) and associated regulatory sequences such as promoters, enhancers, introns, signal sequences, etc. Other sequences to produce compounds that increase efficient production, enhanced stability or are involved in biological activity of the compound can be included in the same or another DNA vector.

In one embodiment the vector is based on the pLXSN, pLNCX, or pLNSX plasmids provided under license from Fred Hutchinson Cancer Research Center.

According to the present invention the delivery of the DNA to the cells of the mammary gland is accomplished by the use of viral-derived particles and packaging cells, which produce these particles, for infusion into the mammary gland through the teat canal. This infusion is a standard veterinary practice and usually involves the use of a cannula for insertion into the teat canal, the cannula being attached to a syringe containing a solution of the packaging cells and viral-derived particles.

It has already been established that such particles derived from retrovirus trans-infect only dividing cells. Thus, the infusion of the particles and the packaging cells takes place when mammary cell division is naturally at a high level. In the present invention heifers at 5 to 7 months pregnancy were used. It would also be possible to use non-pregnant mammals treated with hormones to induce mammary cell division and lactation prior to particle and cell infusion. However, this method would involve additional handling of the animal and thus is not preferred.

Other types of viral-derived particles and associated packaging cell lines, such as those based on adenovirus, Epstein-Barr virus, or other viruses can also be used. These non-retroviral derived particles can infect non-dividing cells. If used in combination with the retroviral derived particles described above, the maximum number of cells will receive the desired DNA. In addition, particles to deliver DNA can be manufactured in vitro and use of these alone or in combination with the above described particles will enhance the number of mammary epithelial cells which incorporate the desired DNA. An example of particles which are constructed in vitro is described or referred to in Morsy and Caskey (1997).

The present invention is applicable to all mammals and is especially applicable to all non-human mammals. Goats, sheep and cows are preferred. Cows with their inherent large volume milk production are particularly preferred.

The packaging cells will attach and survive for a period of time within the mammary gland. The reason for the presence of the cells is to supply a continuous source of the viral-derived particles to trans-infect the maximum number of mammary epithelial cells. Both the packaging cells and the viral-derived particles are eventually destroyed in the mammary gland; however, considering the fragile nature of the particles in vitro, they are likely destroyed within days. The cells, by contrast, may persist much longer. When cells were infused into the udder, and the udder subsequently flushed and assayed for the presence of cells (dead and alive), most of the cells could not be flushed out. Cells were seen in the wash for 3 days after infusion; of those cells that were flushed out, a large majority remain viable, suggesting that most of the cells have become attached to the udder. In prior art methods (for example Archer et al. 1994), the particles are infused into the udder approximately every two days for two weeks. In the present invention no subsequent infusions are necessary. Thus an advantage of the present invention over the prior art is a reduction in the handling of the animal.

In prior arts methods (for example, Archer et al. 1994), large scale tissue culture was required to supply sufficient numbers of particles for multiple infusions. An advantage of the present invention over the prior art is that preparation of a large number of particles is not required.

In prior arts methods (for example, Archer et al. 1994), the preparation of a stock solution of viral-particles required ultra-centrifugation and resuspension of the particles. A further advantage of the present invention is that no ultra-centrifugation is involved. Centrifugation and other handling techniques can destroy the relatively fragile particles. In the present invention, handling of the particles is minimal, increasing the probability that the particles present will remain intact and useful.

The above cited advantages are in addition to the improvement in yield of the compound in the milk, which has already been described above.

This method can be used alone or in combination with other methods of the present invention to increase the incorporation of DNA from the viral-derived particles. The additional methods of the present invention are all designed to ensure that the viral-derived particles are correctly positioned to trans-infect the mammary epithelial cells.

In one embodiment, the teat canal and udder is first emptied by milking or under negative pressure. Then the udder is flushed with an osmotically-balanced solution which is infused into the teat canal and udder until the udder is full. This solution is removed by milking or under negative pressure and the desired suspension is infused into the udder. In an alternative procedure, the teat canal is not emptied first but is directly filled with an osmotically-balanced solution which is then removed by milking or under negative pressure.

Flushing of the udder serves two purposes; it removes the thick, secreted fluid that is normally present and it forces open the ductwork to allow better access of the packaging cells and viral-derived particles which will be inserted in the next step of the procedure. An example of a suitable osmotically-balanced solution includes saline solution, but can include any other buffered solutions, and also can include the packaging cell grown medium.

External massage applied several times a day to the mammary gland improves the circulation of the viral-derived particles and results in more secretory cells in the mammary gland being exposed to the viral-derived particles and thus more cells will incorporate the DNA carried in these particles.

In another embodiment, the packaging cells are grown on a commercially available matrix (designed to support growth and replication of tissue culture cells). This solid support matrix can include gelatin, glass, collagen or plastic beads. Cytodex beads or Cultisphere (purchased from Sigma) are two specific examples of useful support means. The beads, with cells adhering to them, are infused into the mammary gland through the teat canal along with a suspension of DNA-containing viral-derived particles. The beads remain in the mammary gland. External massage applied several times a day to the mammary gland recirculates the beads and helps to distribute the viral-derived particles that are produced by the packaging cells growing on the beads. The presence of the packaging cells on beads also ensures the continuous presence of many more DNA-containing viral-derived particles. Concomitantly more secretory cells in the mammary gland will incorporate the DNA carried within these viral particles and the production of the desired protein will increase accordingly. The beads and any cells remaining on them will eventually be removed when milking is begun.

In another embodiment, the infusion of cells (with or without growth on beads) and viral-derived particles containing the desired DNA is followed by infusion of a substance which is more dense than the water-based suspension fluids, used for cell infusion, such as growth medium (Dulbecco's modified Eagle's medium [DMEM], phosphate buffered saline [PBS], etc.). This dense fluid, which in one example is composed of silicone, displaces the aqueous solutions containing the packaging cells and the viral-derived particles upwards into the ductwork of the mammary gland. This prevents collection of the packaging cells in the cistern of the udder and positions the viral-derived cells and the viral-derived particles up into the ducts of the mammary gland. Thus, the viral-derived particles are positioned near the dividing cells in the alveoli of the mammary gland and allow more of the DNA carried in the viral-derived particles to be incorporated. Any physiologically compatible inert fluid that has a density greater than that of the infusion solution can be used according to this embodiment of the present invention.

Thus, the present invention consists of the following procedure, which can be used alone or in combination with optional methods of the present invention, to deliver heterologous DNA to milk producing cells. In this procedure the following steps occur:

1) A vector containing the desired DNA sequence(s) is constructed and is transfected by standard means into a packaging cell line.

2) A solution containing the packaging cell line, producing viral-derived particles containing the desired DNA sequence(s), and viral-derived particles, is infused into the mammary gland through the teat canal. The packaging cells attach to the epithelial cells of the mammary gland, remain viable and produce viral-derived particles.

3) The DNA becomes incorporated into the secretory cells of the mammary gland.

4) The milk containing the product induced by addition of the desired DNA is milked from the cistern. The product is purified from the milk or the milk, containing the product, is consumed.

The basic technique can be modified by the addition of one or more of the following steps:

1) The udder is flushed with an osmotically-balanced solution.

2) The packaging cells are grown on a matrix designed to support proliferation of eukaryotic cells, such as Cytodex beads, and then infused through the teat canal. The cells will remain in the mammary gland and continue to produce viral-derived particles for a period of at least 3 days.

3) After infusion of the packaging cells (either as a suspension or grown on a matrix), a compound which is denser than aqueous solutions, such as silicone, is infused into the mammary gland to force the aqueous solutions carrying the packaging cells and viral-derived particles up and into the region of the mammary gland where the DNA can be incorporated into the milk producing cells. The dense compound, if it has been added, and any unattached cells as well as the matrix, if used, is removed from the mammary gland cistern by milking at an appropriate time after infusion. An appropriate time is defined as after the majority of packaging cells attach and after there is sufficient production of viral-derived particles. An example of an appropriate time would be at least 3 days, however shorter or longer periods may also be used. The packaging cells which are not removed at this time die and are removed by the recipient's natural mechanisms.

4) External massage applied several times a day to the mammary gland will recirculate the viral-derived particles and the packaging cells, provided either as a suspension or grown on a matrix. This helps to distribute the viral-particles and the cells and increases the incorporation of the DNA carried in these particles into the secretory cells.

While this invention is described in detail with particular reference to preferred embodiments thereof, said embodiments are offered to illustrate but do not limit the invention.

EXAMPLES

Example 1

Preparation of Plasmids Carrying the Desired Gene and Various Control Sequences for use in Retroviral Particle Delivery to Bovine Mammary Epithelial Cells As a system to transfect the mammary epithelial cells with a desired gene, the PG13 packaging cell line was acquired under license from Fred Hutchinson Cancer Research Center. This system was used because it produces retroviral particles containing the gibbon ape leukemia virus envelope (Galv) which facilitates transfection of bovine cells. To package the desired gene "X" into retroviral particles, the plasmids, pLXSN, pLNCX, pLNSX and pLN, also were acquired under license from Fred Hutchinson Cancer Research Center.

Modifications of Plasmids:

In order to have an alternative method to select cell clones containing the desired gene, we replaced the neomycin (neo) gene with the hygromycin (hyg) gene in pLXSN, pLNSX and pLNCX. This was done by long-range PCR-amplification of the region around the neo gene then ligating the PCR product with the hyg gene which was amplified from the plasmid pREP4 (purchased from Invitrogen). The resulting plasmids were called pLXSH, pLHSX and pLHCX where "L" represents the Moloney murine virus long terminal repeat (LTR) acting as a promoter, "S" is the SV40 promoter and "C" is the cytomegalovirus promoter region.

To put the desired gene, "X", under the control of a constitutive promoter, the cytomegalovirus promoter region in pLNCX and pLHCX was removed by restriction digestion and replaced with the beta actin promoter to make pLNAX and pLHAX. The beta actin promoter sequence was derived using PCR from the pJ6Ω plasmid purchased from ATCC (catalog no. 37723).

In order to avoid transcription interference between the gene used for selection and the gene used to produce the desired protein, transcription from both genes was coupled by replacing the SV40 promoter from the plasmids pLXSN and pLXSH with an internal ribosomal entry site (IRES). The resulting plasmids, pLAiN and pLAiH, express both the selection gene and the inserted gene under the same (LTR) promoter. The IRES in these plasmids provides the translation initiation site within the transcript, allowing the downstream gene product to be produced. The IRES used here is identical to the IRES found in the plasmid pIRES1neo purchased from Clontech. The sequences for pLAiN and pLAiH, where A in this case is chicken amylase but which can be any desired protein, are shown in SEQ ID No:1 and SEQ ID No:2, respectively.

In order to increase retroviral titre or stability of the transcript, or to increase the expression level of the desired gene during lactation, or to allow translation of more than one protein from the same transcript, the basic plasmid, pLNCX, was modified. In one modification, the selection gene was removed to minimize the size of the resulting plasmid, pLX. In another modification, the CMV promoter was replaced with the murine mammary tumour virus (M) LTR promoter to improve transcription of the resulting plasmid, pLNMX, during lactation. The sequence for pLNMX is shown in SEQ ID No:3.

In another modification, a wild-type IRES was modified so that the ATG codon at position 10 is destroyed and the sequence downstream of the ATG codon at position 11 codes for the desired gene, "X", in a plasmid such as pLNMi$_2$X. The sequence for this IRES modification (i$_2$) is included within the sequence for pLNMi$_2$X, shown in SEQ ID No:4.

Example 2

Preparation of Cell Clones Producing Viral-derived Particles Carrying the Chicken Amylase Gene as a "Marker" Protein The two packaging cell lines used in this experiment were purchased from ATCC, PA317 (catalog no. CRL-9078) and PG13 (catalog no. CRL-10686). A description of both PA317 and PG13 and their use can be found in Miller et al. 1990.

To develop and optimize the transfection of mammary epithelial cells using the retroviral particle delivery system, we used a stable and readily detectable marker protein, chicken amylase, in some experiments. Chicken amylase migrates at a unique position by native gel electrophoresis and can be differentiated from bovine or other amylases. To produce a PG13-derived cell line (a clone) producing retroviral particles which carried chicken amylase under the control of the beta actin promoter, the following procedure was done.

The pLH(A)amy plasmid with hygromycin (H) driven by the LTR promoter and with amylase (amy) driven by the beta actin promoter (A), was produced by standard recombinant techniques. pLH(A)amy was transiently transfected by the calcium phosphate technique into the PA317 packaging cell line. The transfected PA317 cells produce viral particles containing the amy RNA into the supernatant. The amphotropic viral envelope protein of these particles allows entry into cells of most species including the PG13 packaging cells in a process called trans-infection. Empirically it has been determined that trans-infection produces PG13 clones with a higher rate of particle production as compared to PG13 clones produced by other means of DNA insertion (particle bombardment, calcium phosphate or liposome transfection). Therefore, the viral-derived particles in the supernatant of the transfected PA317 cells were used to trans-infect the PG13 packaging cell line. The resulting clones were selected using 700 ug/ml hygromycin in DMEM with 10% fetal bovine serum (FBS) and 1% penicillin/streptomycin for 14 days. Clones were picked using cloning rings and grown as separate cell lines.

These PG13 amy clones were tested for amylase production by native gel electrophoresis of α-amylase. The α-amylase samples in loading buffer (0.1 M tris-borate pH 8.5, 10% sucrose, 10 mM magnesium chloride) were electrophoresed for 3–4 hours at 250 volts, with cooling, on a 5.5% acrylamide gel containing 0.1 M tris-borate pH 8.5. The electrophoresis buffer was 0.1M tris-borate pH 8.5. The gel was then placed with gentle shaking for 1 h at room temperature in a solution of 2% soluble starch, 10 mM calcium chloride, 50mM tris-HCl pH 7.5. The gel was briefly rinsed in water, then placed in a dilute solution of iodine ($I_2$:KI: water is about 1:2:2000) until the amylase signal shows as a clear band on the gel.

All packaging cells produce filled retroviral particles which contain the desired gene and empty particles which do not carry the desired gene. To increase the number of filled retroviral particles, hygromycin-resistant PG13 amy clones producing high amounts of amylase were supertransfected with a second plasmid, pLN(A)amy, which also carried the amylase gene but which has neomycin as the clone selection agent. In this procedure, first pLN(A)amy was transfected into the PA317 cell line by the calcium phosphate procedure, and then the viral-derived particles in the supernatant of the transfected PA317 amy-containing cells were used to trans-infect a PG13/pLH(A)amy clone. The PG13/pLH(A) clone which was supertransfected was chosen on the basis of high amylase production. Superclones, containing both pLN(A) amy and pLH(A)amy sequences were obtained by selecting in the presence of 1000 ug/ml G418 and 700 ug/ml hygromycin as described above. The surviving clones were picked and grown up for further testing. Although a marker protein, amylase, was used in these experiments to optimize filling of particles, it is obvious that the same procedure can be done where another protein, such as a pharmaceutical protein, is used instead of the amylase.

The superclones producing the highest levels of amylase were analyzed for particle production by the following method. For each clone to be tested, the supernatant containing viral-derived particles was used to trans-infect HeLa 229 (human cervical carcinoma) (purchased from ATCC catalog no. CCL-2.1) and Et2 (bovine mammary) cells (provided by Dr. Boris Zavizion, University of Vermont, Burlington, Vt.). Depending on the resistance gene contained in the plasmid, the trans-infected cells were treated with either 700 ug/ml hygromycin or 1000 ug/ml neomycin, or both, and the resulting colonies were counted. Each colony is the result of one infective (filled) particle. The clone producing the highest number of colonies was selected to be grown for subsequent infusion into the heifer udder. In the specific example shown in FIG. 1, clone 10 produced the highest number of viral-derived particles and was designated as PG13/LH/LN(A)amy.

Before a clone can be infused into the udder, it must be tested to determine that it does not produce replication-competent (called "helper") virus. Gene therapy is based on the assumption that the viral-derived particles can carry the desired DNA (i.e. cDNA for amylase or another protein) into the target cell but that once in the cell, the virus cannot reproduce itself. There are two methods to check if helper virus is being produced by the trans-infected packaging cell line. These are described in detail in Cepko, 1992. The first method is to analyze the supernatant of the HeLa and Et2 cells for horizontal spread of hygromycin and/or neomycin resistance. The second method is to look for the presence of reverse transcriptase above background levels in the supernatant of the trans-infected HeLa and Et2 cells. If trans-infection with the supernatant from HeLa and Et2 cells does not produce hygromycin and/or neomycin resistant colonies and if there is no reverse transcriptase above the level found in control cells, then it can be assumed that the particle producing clone, in this case PG13/LH/LN(A)amy, is not producing "helper" virus and therefore can be used for infusion into the udder. We followed the procedures detailed in the Cepko reference and found neither colony nor reverse transcriptase production.

Example 3

Infusion of Clones Producing Retroviral-derived Particles Which Carry a Desired Gene Such as the Amylase Marker Protein In one example, the cell clone PG13/LH/LN(A)amy, which expresses chicken amylase as a marker protein, was infused into the udder of a 7 month pregnant heifer, #99. Before infusion with the cell clone, each quarter of the udder was flushed with 250 ml of saline solution at 37° C. using the catheter portion of an angiocath G-18 catheter attached to a 140 cc Monoject syringe with a Luer lock attachment (both purchased from CDMV, Saint-Hyacinthe, Quebec). The infusate was then milked out and measured to determine the volume of cell solution which could be administered to this particular quarter of this specific heifer.

Two superclones, designated as PG13/LH/LN(A)amy Clone 10 and PG13/LH/LN(A)amy Clone 12, were grown in standard tissue culture flasks until the total cell number (in an appropriate number of flasks) was >$2\times10^8$ cells/clone. The cells were trypsinized, counted and resuspended at $1\times10^8$ cells in 250 ml DMEM without serum but containing 80 ug/ml of Polybrene to facilitate particle adsorption to the mammary epithelial cells.

The udder has four separate quarters. The left front quarter was left untouched as a negative control (LF−). The front right quarter was flushed with saline and infused with 250 ml DMEM plus 80 ug/ml Polybrene but with NO cells added and served as a negative control (RF−). The right hind quarter was infused with $1\times10^8$ Clone 12 cells in 250 ml DMEM plus Polybrene (RH+) and the left hind quarter was infused $1\times10^8$ Clone 10 cells in 250 ml DMEM plus Polybrene (LH+). The infusate was not removed. The udder was massaged 3 times a day, morning, noon and night, to help to distribute the cells which tend to settle into the cistern of the udder. Three weeks post infusion, the udder was "stripped" (all secretions were milked by hand from each quarter) which removed about 7 to 10 ml per quarter of a viscous, serum-like fluid. This was designated as "early premilk". Eight weeks post infusion the udder was stripped again, producing about 25 ml per quarter of a slightly cloudy, viscous fluid designated as "late premilk". The samples from the right front control quarter RF(−) and the two infused quarters, the right hind, RH(+) and the left hind, LH(+) were analyzed for the presence of active amylase as previously described (see FIG. 1).

FIG. 1 shows that in the early premilk sample, amylase is present in both infused quarters (RH) and (LH) while the control quarter (RF) contains no amylase. In the late premilk, the negative control quarter (RF) continues to show no amylase activity. Clone 10, left hind quarter, shows the highest amylase activity. Clone 12, right hind quarter, has decreased activity compared to the early premilk sample, but a small amount of amylase activity was detected. The samples loaded represent equal volumes (100 ul/lane) of the premilk samples. No attempt was made to load equal amounts of protein. The apparent reduction in the amount of amylase present between early and late premilk samples is caused by increased volume of the late premilk samples relative to the volume of the early premilk samples.

Example 4

Preparation of a Clone Producing Viral-derived Particles That Carry the tPA Gene and Infusion of This Clone Into the Udder of a Pregnant Heifer Tissue plasminogen activator (tPA) is used to treat heart attack and stroke by dissolving blood clots. We selected human tPA to be the first pharmaceutical product to be produced by our method in bovine milk. The ptPA-K plasmid, containing the mutated cDNA sequence for human tPA (where the amino acids KHRR 296–299 was mutated to AAAA. i.e. the "K" mutation), was purchased from ATCC (American Type Culture Collection, catalog no. 68059). Two additional mutations were incorporated into ptPA-K to form ptPA-TNK: the amino acid threonine at position 103 was mutated to asparagine (the "T" mutation), and the amino acid asparagine at position 117 was mutated to glutamine (the "N" mutation). The tPA amino acid sequence and a description of the above modifications can be found in Pennica et al. 1983. Both mutations were produced by using mismatched oligonucleotides containing the altered nucleotide sequence as primers for PCR amplification. The tPA-TNK gene was subsequently excised by restriction digestion and ligated into the pLXSH plasmid to make pL(tPA)SH.

The resulting PG13(tPA) clones were analyzed for tPA production by colorimetric determination using Spectrozyme (#444 purchased from American Diagnostica Inc.). Clones which showed high levels of tPA were then checked for production of filled particles by colony counts (as described previously) and were safety checked to insure that no replication competent virus was being produced and that there was no reverse transcriptase production above that found as background in HeLa or ET2 cells. None of the clones tested produced replication competent virus by either of these tests. The clones with the highest particle production and highest level of tPA production were selected to be grown for infusion into the udder. In the following example, clone PG13/L(tPA)SH-1, was chosen for infusion into the udder.

In one example, Clone 1 (PG13/L(tPA)SH-1), which produces tPA, was infused into the udder of a seven and a half month pregnant heifer, #90 and into the udder of a six and a half month pregnant heifer, #56. Before infusion of the clone and particles produced by it, each quarter of the udder in both heifers was flushed with 250 ml of saline as described in Example 3. After milking out the saline, the right rear (RR) quarter of heifer #90 received $2.5\times10^7$ cells of Clone 1 plus 80 ug/ml Polybrene in 250 ml of DMEM without serum while the right front (RF) quarter received $1\times10^8$ cells of Clone 1 plus 80 ug/ml Polybrene in 250 ml of DMEM without serum. The left front (LF) quarter received 250 ml of DMEM as a control while the left rear (LR) quarter was the untreated control. Heifer #56 received $2.5\times10^7$ cells of Clone 1 plus 80 ug/ml Polybrene in 250 ml of DMEM without serum in the left front quarter (LF+) and $1\times10^8$ cells of Clone 1 plus 80 ug/ml Polybrene in 250 ml of DMEM without serum in the right rear quarter (RR+). The right front quarter received 250 ml of DMEM as a control (RF−) while the left front (LF−) quarter was the untreated control. In both heifers, the infusate was not removed and the udder was massaged three times daily to help distribute the cells and particles up into the ductwork.

Four weeks post-infusion, the four quarters of both heifers were stripped to remove 5 to 9 ml of the viscous, serum-like premilk fluid. The premilk samples from treated and control quarters of both heifers were analyzed for the presence of tPA by Western blotting. A Western blot showing the tPA results obtained from the best quarter of each heifer is shown in FIG. 2.

For Western blotting, the premilk samples were adjusted to pH 4.5 with acetic acid and centrifuged at 13,000×g to pellet the "curd" fraction. The "whey" fraction contained in the supernatant was collected and diluted 1:5 with sample buffer. Samples of 20 ul were loaded onto a 7.5% SDS PAGE gel. To detect tPA, the gel was transferred to nitrocellulose and then blocked overnight in 5% bovine serum albumin (BSA). The blot was incubated for 2 hours with a polyclonal antibody to tPA, #385R, purchased from American Diagnostica, diluted 1:500 with PBS followed by extensive washing in PBS. The secondary antibody, horseradish peroxidase goat-anti-rabbit, diluted 1:5000 in PBS, was incubated with the blot for one hour then extensively washed. Detection of antibody staining of tPA was by enhanced chemiluminescence (ECL) Amersham Detect Kit. Specificity of the primary antibody was previously determined by Western blotting a control sample of commercial tPA purchased from American Diagnostica.

Figure 2:
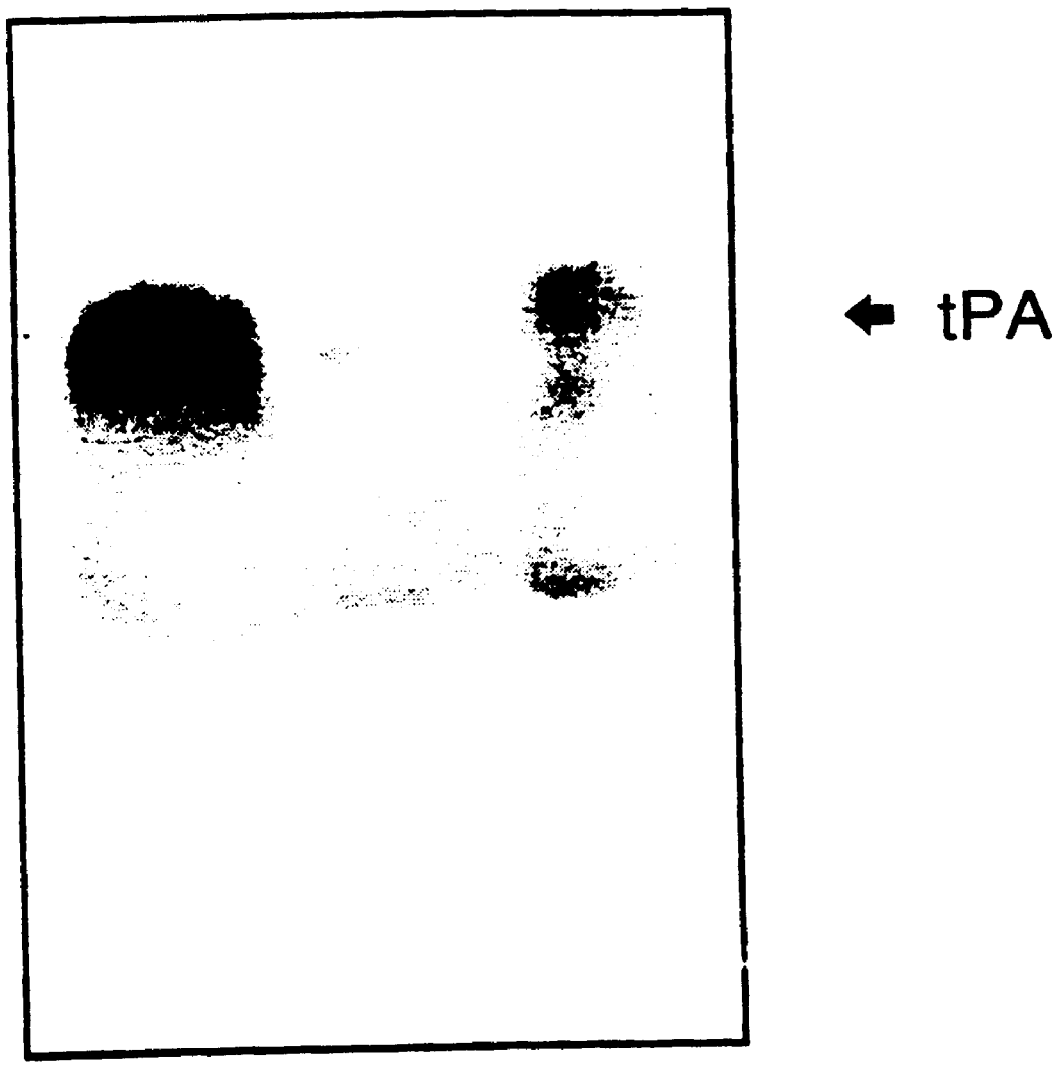
FIG. 2 is a Western blot showing the presence of tPA in an udder infused with Clone 1. Lane 1, premilk from treated quarter (LH+) of cow #56; Lane 2, premilk from control quarter (LF−) of cow #56; Lane 3, premilk from treated quarter (RF+) of cow #90.

Results of Western blotting samples obtained from the untreated control quarter (LF−) and from one treated quarters of each heifer are shown in FIG. 2. Lane 1 shows a strong tPA band in the premilk from the treated (LH+) quarter of heifer #56. The middle lane, lane 2, contains premilk from the (LF−) control quarter of cow #56. Lane 3 shows a tPA band in the premilk from the treated (RF+) quarter of heifer #90. A faint smear in all 3 sample lanes is the result of non-specific binding of the antibody to an unidentified protein and should be disregarded.

Example 5

Determination of Viability and Attachment of 3T3 Cells to the Surface of the Bovine Udder.

The cells used in this experiment were 3T3 cells (purchased from ATCC, catalog no. CCL-92) which had been transfected with luciferase as a marker protein. These 3T3 cells are essentially identical to the PG13 packaging cells except that the 3T3 cells have not been transfected with the retroviral genes that are found in the packaging line.

Three quarters of the udder of a 5 month pregnant heifer and three quarters of the udder of a 7 month pregnant heifer were flushed with saline solution at 37° C. using a standard veterinary infusion apparatus. The saline was then milked out and measured to determine what quantity of medium with or without cells could be infused into that particular quarter. In both heifers, one udder quarter was left untreated as a negative control; a second quarter received only DMEM, the third quarter received $1 \times 10^6$ cells suspended in an appropriate amount of DMEM, and the fourth quarter received $1 \times 10^7$ cells also suspended in an appropriate amount of DMEM. The quarters were then milked to produce about 10 ml of fluid at 3 hours, 24 hours, and 72 hours post-infusion.

The fluid obtained by milking was divided in half. One portion was cultured under standard conditions for 3T3 cells to determine if the cells were viable. The second portion was used in a luciferase assay to count the approximate number of 3T3-luciferase cells per ml in the fluid. A control was run simultaneously using known numbers of 3T3-luciferase cells and a curve drawn to determine the correlation of luciferase intensity with cell number.

The results of two experiments indicated that the highest number of cells were found 3 hours post infusion and progressively fewer cells were found in the fluid milked from the udder at 24 and 72 hours. However the cells which were milked out at 72 hours were viable. This is evidence that the cells are attaching to the udder surface and that those cells which were unattached (and therefore could be milked out of the udder) remained viable for the period of the experiment. This suggests that the 3T3 cells are not quickly destroyed by the factors in the environment of the udder. Thus PG13(tPA) cells can be expected to remain viable for at least a period of 3 days during which time they will continue to produce viral-derived particles and can therefore trans-infect a substantial number of mammary epithelial cells.

TABLE 1

Attachment of 3T3 cells to udder walls

| Udder Quarter | Treatment | Attachment of 3T3 cells to udder interior at: | | |
|---|---|---|---|---|
| | | 3 hours post-infusion | 24 hours post-infusion | 72 hours post-infusion |
| left hind | no treatment | – | – | – |
| left front | medium only | – | – | – |
| right hind | $1 \times 10^6$ cells | – | +/– | + |
| right front | $1 \times 10^7$ cells | +/– | +/+ | +/+ |

Example 6

Infusion of 3T3 Cells Grown on a Solid Support Means

The cells used in this experiment were 3T3 cells, as described in Example 2.

In this example however the cells were grown on Cytodex beads.

The cells growing on beads were infused into the udder of a 7 month pregnant heifer and subsequently removed 1, 2 and 3 days later as described in Example 2. Cells were removed from beads and viability was determined by Trypan blue exclusion. The cells remained viable for the entire period.

Example 7

Use of Silicone to Displace the Cells and Viral-derived Particles

The cells used in this experiment were 3T3 cells, as described in Example 3. The volume of the solution containing the cells and viral-derived particles was reduced by 50 ml, 25 ml, or 10 ml but the overall number of the cells remained constant.

After the solution was infused into the udder, as described in the preceding examples, approximately 50 ml, 25 ml or 10 ml of silicone was infused into the mammary gland, using the methods previously described.

After three days the silicone was removed from the cistern by milking. No reaction to the silicone was noted.

All scientific publications and patent documents are incorporated herein by reference.

References:

Archer, J. S., W. S. Kennan. M. N. Gould, R. D. Bremel. 1994. Human growth hormone (hGH) secretion in milk of goats after direct transfer of the hGH gene into the mammary gland by using replication-defective retrovirus vectors. Proc. Natl. Acad. Sci. USA, 91:6840–6844.

Cepko. C. 1992. Transduction of genes using retrovirus vectors. In: Short Protocols in Molecular Biology, 2nd edition. Ed. F. M. Ausubel, R. Brent, R. E. Kingston, D. D. Moore, J. G. Seidman, J. A. Struhl, Pub. by John Wiley & Sons. New York, N.Y. pp 9–30 to 9–45.

Furth, P. A., A. Shamay, R. J. Wall, L. Henninghausen. 1992. Gene transfer into somatic tissues by jet injection. Analyt. Biochem. 205:365–368.

Miller, A. D., D. G. Miller, J. V. Garcia, C. M. Lynch. 1990. Use of retroviral vectors for gene transfer and expression. Meth. Enzymol. 217: 581–599.

Morsy, M. A. and C. T. Caskey. 1997. Safe gene vectors made simpler. Nature Biotech. 15:17.

Pennica, D, W. E. Holmes, W. J. Kohr, R. N. Harkins, G. A. Vehaar, C. A. Ward, W. F. Bennett, E. Yelverton, P. H. Seeburg, H. L. Heyneker, D. V. Goeddel. 1983. Cloning and expression of human tissue-type plaminogen activator cDNA in E. coli. Nature 301: 214–221.

Thierry, A. R., Y. Lunardi-Iskandar, J. L. Bryant, P. Rabinovich, R. C. Gallo, L. C. Mahan. 1995. Systemic gene therapy: Biodistribution and long-term expression of a transgene in mice. Proc. Natl. Acad. Sci. USA. 92:9742–9746.

The present invention has been described with regard to preferred embodiments. However, it will be obvious to persons skilled in the art that a number of variations and modifications can be made without departing from the scope of the invention as described in the following claims.

The embodiments of the invention in which an exclusive property or privilege is claimed are defined as follows:

1. A method of producing a trans-somatic mammal, wherein said method provides the incorporation of a DNA sequence into the secretory cells of the mammary gland to alter the composition of the milk, wherein said method comprising the steps of:
   a) providing a retroviral vector containing a DNA sequence encoding a polypeptide;
   b) packaging said retroviral vector in a cell line to produce retroviral particles;
   c) preparing a solution comprising the retroviral particles and cell line producing said retroviral particles; and
   d) delivering said solution into the mammary gland to allow the incorporation of the DNA into the secretory cells of the mammary gland, wherein a substance, with a density higher than the density of the solution comprising the retroviral particles and cell line producing said retroviral particles, is delivered into the mammary gland after the delivery of the solution comprising the retroviral particles and cell line producing said retroviral particles, wherein said substance displaces the solution upwards in the mammary gland.

2. The method of claim 1, wherein the method further comprises the step of flushing the mammary gland with an osmotically-balanced solution prior to delivering said solution into the mammary gland.

3. The method of claim 2, wherein the method further comprises the step of externally massaging the mammary gland several times a day after delivering said solution comprising the retroviral particles and cell line producing said retroviral particles into the mammary gland.

4. The method of claim 2, wherein the method further comprises the step of growing the cells producing said retroviral particles on a solid support means, and the solution comprising the retroviral particles and cell line producing said retroviral particles further comprises the cells on said support means and the retroviral particles.

5. The method of claim 4, wherein the method further comprises the step of externally massaging the mammary gland several times a day after delivering said solution comprising the retroviral particles and cell line producing said retroviral particles into the mammary gland.

6. The method of claim 4, wherein the solid support means is a matrix comprising collagen coated dextran beads.

7. The method of claim 2, wherein the osmotically-balanced solution is a saline solution.

8. The method of claim 1, wherein the polypeptide is a pharmaceutical.

9. The method of claim 8, wherein the pharmaceutical is a compound selected from the group consisting of: a tissue plasminogen activator, an antibody, a blood clotting factor, galactosyltransferase, a growth factor, an oncoprotein, a hormone, a milk protein, a hormone receptor, a tumor suppressor protein, a vaccine and an erythropoietin.

10. The method of claim 9, wherein the pharmaceutical is a tissue plasminogen activator.

11. The method of claim 1, wherein the retroviral vector is transiently transfected into PA317 cells; the resulting particles are harvested and trans-infected into PG 13 cells.

12. The method of claim 1, wherein the retroviral vector is selected from the group consisting of pL(X)SH, pL(X)SN, pLNS(X), pLHS(X), pLNC(X), pLHC(X), pLNA(X) and pLHA(X); wherein "A" is the beta actin promoter, "L" is the moloney murine virus long terminal repeat (LTR), "S" is the SV40 promoter, "C" is the cytomegalovirus promoter, "N" is the neomycin resistance gene, "H" is the hygromycin resistance gene, and "X" is a DNA sequence encoding a polypeptide.

13. The method of claim 1, wherein the retroviral vector is selected from the group consisting of pL(X)iN and pL(X)iH; wherein "i" is an internal ribosomal entry site (IRES), "L" is the moloney murine virus long terminal repeat (LTR), "N" is the neomycin resistance gene, "H" is the hygromycin resistance gene, and "X" is a DNA sequence encoding a polypeptide.

14. The method of claim 1, wherein the retroviral vector is pLNM(X); wherein "M" is a mouse mammary tumor virus promoter, "L" is the moloney murine virus long terminal repeat (LTR), "N" is the neomycin resistance gene and "X" is a DNA sequence encoding a polypeptide.

15. The method of claim 1, wherein the retroviral vector is pLNMi$_2$(X); wherein "M" is a mouse mammary tumor virus promoter, "L" is the moloney murine virus long terminal repeat (LTR), "i$_2$" is a modified wild type internal ribosomal entry site, "N" is the neomycin resistance gene and "X" is a DNA sequence encoding a polypeptide.

16. The method of any one of claims 12 to 15, wherein "X" is a DNA sequence encoding a tissue plasminogen activator.

17. The method of claim 1, wherein the solution is an aqueous solution.

18. The method of claim 1, wherein said substance is a silicone substance.

19. The method of claim 1, wherein the retroviral vector is produced in vitro.

20. The method of claim 1, wherein the retroviral vector is produced in vivo.

* * * * *